(12) United States Patent
Krishnan et al.

(10) Patent No.: US 7,537,890 B2
(45) Date of Patent: May 26, 2009

(54) METHODS OF PERFORMING BIOCHEMICAL REACTIONS IN A CONVECTIVE FLOW FIELD

(75) Inventors: Madhavi Krishnan, Ann Arbor, MI (US); Victor Ugaz, Ann Arbor, MI (US); Mark Burns, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 25 days.

(21) Appl. No.: 10/678,805

(22) Filed: Oct. 3, 2003

(65) Prior Publication Data

US 2005/0074782 A1    Apr. 7, 2005

(51) Int. Cl.
*C12Q 1/68* (2006.01)
*C12P 19/34* (2006.01)

(52) U.S. Cl. .......................................... 435/6; 435/91.2
(58) Field of Classification Search .................... 435/6, 435/91.2
See application file for complete search history.

(56) References Cited

U.S. PATENT DOCUMENTS

| | | | | |
|---|---|---|---|---|
| 4,608,222 | A | 8/1986 | Brueckner | 376/104 |
| 4,683,195 | A | 7/1987 | Mullis et al. | 435/6 |
| 4,683,202 | A | 7/1987 | Mullis et al. | 435/91 |
| 4,965,188 | A | 10/1990 | Mullis et al. | 435/6 |
| 5,091,328 | A | 2/1992 | Miller | 437/52 |
| 5,169,918 | A * | 12/1992 | Tomishima et al. | 526/344.2 |
| 5,626,764 | A | 5/1997 | Burns et al. | 210/661 |
| 5,958,349 | A * | 9/1999 | Petersen et al. | 422/198 |
| 6,048,734 | A | 4/2000 | Burns et al. | 436/180 |
| 6,057,149 | A | 5/2000 | Burns et al. | 435/287.2 |
| 6,130,098 | A | 10/2000 | Burns et al. | 436/180 |
| 6,271,021 | B1 | 8/2001 | Burns et al. | 435/287.2 |
| 6,379,929 | B1 | 4/2002 | Burns et al. | 435/91.2 |
| 6,515,857 | B2 | 2/2003 | Ford et al. | 361/687 |
| 2002/0127152 | A1* | 9/2002 | Benett et al. | 422/131 |
| 2003/0077599 | A1* | 4/2003 | Sogard | 435/6 |
| 2004/0209331 | A1* | 10/2004 | Ririe | 435/91.2 |

OTHER PUBLICATIONS

Krishnan et al. PCR in a Rayleigh-Benard Convection Cell. Science, vol. 298, p. 793, Oct. 25, 2005.*
Ecke et al. International Journal of Engineering Science, vol. 36, pp. 1471-1480, 1998.*
Vorobieff et al. Physics D, vol. 123, pp. 153-160, 1998.*
Selvaganapathy et al. Proceedings of the IEEE, vol. 91, No. 6, pp. 954-974, Jun. 6, 2003.*
Adamson, A. W.,*Physical Chemistry of Surfaces*, 5th ed., Wiley, NY,NY, 395-399 (1990).
Chamberlain et al.,"New RNA Polymerase from *Escherichia coli* infected with Bacteriophage T7," *Nature*, 228:227-231 (1970).
Doty et al.,"Strand Separation and Sepecific Recombination in Deoxyribonucleic Acids:Physical Chemical Studies", *Proc.Nat. Acad.Sci.*, U.S.A. 46:461-477 (1960).
Hayashi et al.,"Restriction of in Vivo Genetic Transcription to one of the Complementary Strands of DNA", *Proc.Nat.Acad.Sci.*, U.S.A. 50: 664-671 (1963).
Innis et al., "DNA sequencing with *Thermus aquaticus* DNA polymerase and direct sequencing of polymerase chain reaction-amplified DNA", *Proc. Natl. Acad. Sci. USA* 85:9436-9440 (1988).
Kacian et al.,"A Replicating RNA Molecule Suitable for a Detailed Analysis of Extracellular Evolution and Replication", *Proc. Natl. Acad. Sci. USA*, 69:3038-3042 (1972).
Kim, E. and Whitesides, G.M., "Imbibition and Flow of Wetting Liquids in Noncircular Capillaries," *J. Phys. Chem. B.*, 101:855-863 (1997).
Kleppe K, et al., "Studies on polynucleotides. XCVI. Repair replications of short synthetic DNA's as catalyzed by DNA polymerases." *J Mol Biol* 56:341-61 (1971).
Lindahl, T., and B. Nyberg,"Rate of Depurination of Native Deoxyribonucleic Acid," *Biochemistry* 11:3610-3618 (1972).
Maniatis, et al.,"Regulation of Inducible and Tissue-Specific Gene Expression," *Science* 236:1237-1245 (1987).
Marmur and Lane,"Strand Separation and Specific Recombination in Deoxyribonucleic Acids: Biological Studies", *Proc.Nat.Acad.Sci.*, U.S.A. 46:453-461 (1960).
Pearson and Lipman,"Improved tools for biological sequence comparison", *Proc. Natl. Acad. Sci.* (U.S.A.) 85:2444-2448 (1988).
Sambrook, J. et al., Molecular Cloning, A Laboratory Manual, 2d Ed. Cold Spring Harbor Laboratory Press, New York, 13.7-13.9.
Smith and Waterman,"Comparison of Biosequences," *Adv. Appl. Math.* 2:482-489 (1981).
Smith and Wilcox, "A Restriction Enzyme from *Hemophilus influenzae*", *J.Mol.Biol.* 51:379-391 (1970).
Southern, "Detection of Specific Sequences Among DNA Fragments Separated by Gel Electrophoresis", *J.Mol.Biol.* 98:503-517 (1975).
Voss, et al.,"The role of enhancers in the regulation of cell-type-specific transcriptional control," *Trends Biochem. Sci.*, 11:287-289 (1986).
Wu and Wallace,"The Ligation Amplification Reaction (LAR)-Amplification of Specific DNA Sequences Using Sequential Rounds of Template-Dependent Ligation," *Genomics*, 4:560-569 (1989).
Zhang, P., et al., "Patterns in spherical Rayleigh-Benard convection: a giant spiral roll and its dislocations" *Phys Rev E Stat Nonlin Soft Matter Phys* 66(5 Pt 2):055203 (2002).

\* cited by examiner

*Primary Examiner*—Gary Benzion
*Assistant Examiner*—Cynthia B Wilder
(74) *Attorney, Agent, or Firm*—Medlen & Carroll, LLP

(57) ABSTRACT

The present invention provides methods and systems for running reactions, in particular, biological reactions and assays, in a Rayleigh-Bénard convection cell. The utilization of Rayleigh-Bénard convection principles for conducting biological or biochemical reactions is a novel application. In order to use Rayleigh-Bénard convection for conducting biological or biochemical reactions it is necessary to create a temperature differential in a solution of reactants.

31 Claims, 21 Drawing Sheets

PLATE HEATED FROM BELOW

ENERGY IS TRANSFERRED FROM BOTTOM TO TOP BY THE
CONVECTION CELLS FORMED IN THE FLUID WHEN
Ra EXCEEDS 1708. THE DIRECTION OF ROTATION OF
TWO ADJACENT CELLS ARE SHOWN IN THE FIGURE

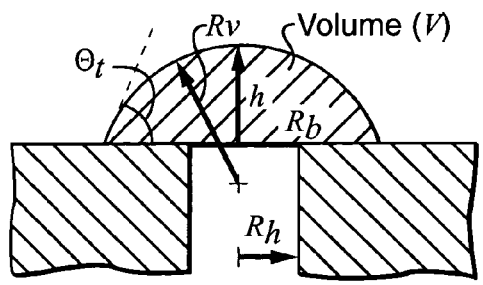
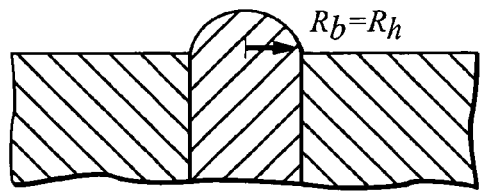
FIG. 7A  FIG. 7B
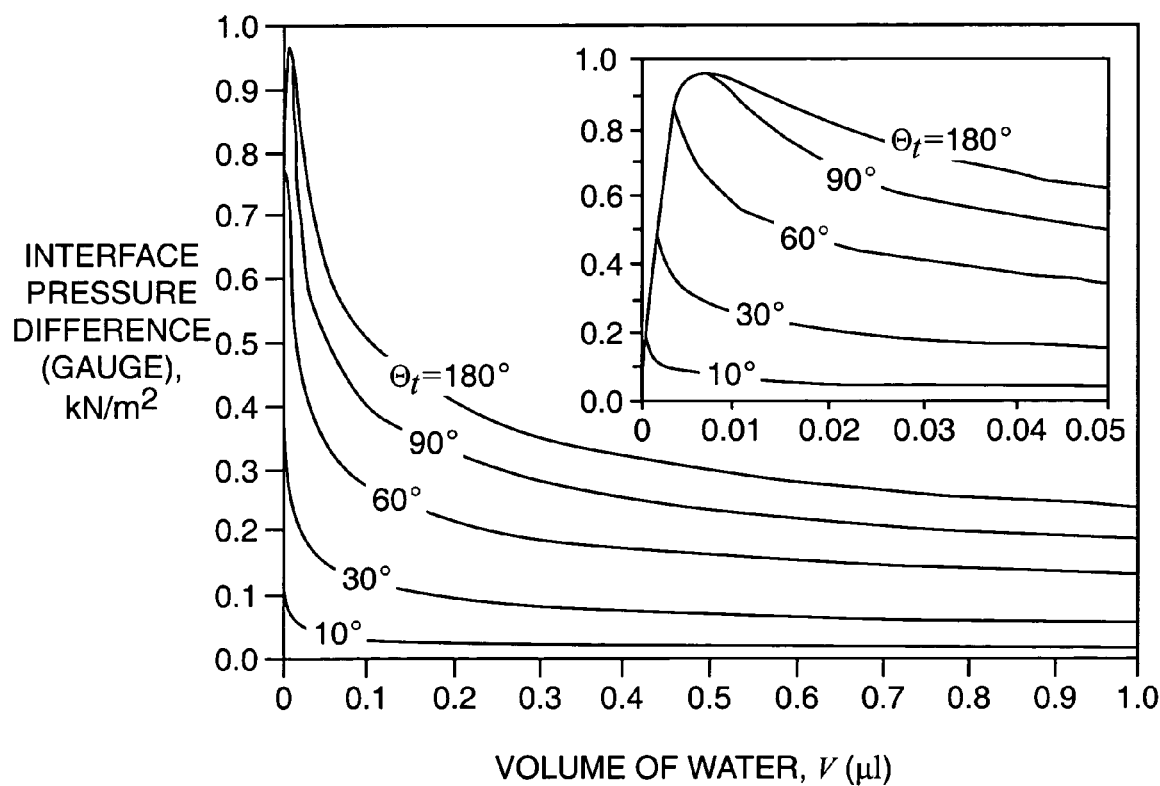
FIG. 7C

US 7,537,890 B2

METHODS OF PERFORMING BIOCHEMICAL REACTIONS IN A CONVECTIVE FLOW FIELD

This invention was made with funding from the National Institutes of Health, under grant nos. K22-HG02297 and P01-HG01984-01. The Government has certain rights in this invention.

FIELD OF THE INVENTION

This invention relates to methods and compositions for the performance of biological and biochemical reactions in convection flow fields. In particular, biological and biochemical reactions are performed under conditions of Rayleigh-Benard convection. A variety of reactions are contemplated, including reactions utilizing temperature changes and temperature cycling.

BACKGROUND

The initial observations of the "hybridization" process, i.e., the ability of two polymers of nucleic acid containing complementary sequences to find each other and anneal through base pairing interaction, by Marmur and Lane, Proc. Nat. Acad. Sci., U.S.A. 46, 453 (1960) and Doty, et al., Proc. Nat. Acad. Sci., U.S.A. 46, 461 (1960), have been followed by the refinement of this process into an essential tool of modern biology. Initial hybridization studies, such as those performed by Hayashi, et al., Proc. Nat. Acad. Sci., U.S.A. 50, 664 (1963), were formed in solution. Further development led to the immobilization of the target DNA or RNA on solid supports. With the discovery of specific restriction endonucleases by Smith and Wilcox, J. Mol. Biol. 51, 379 (1970), it became possible to isolate discrete fragments of DNA. Utilization of immobilization techniques, such as those described by Southern, J. Mol. Biol. 98, 503 (1975), in combination with restriction enzymes, has allowed for the identification by hybridization of singly copy genes among a mass of fractionated, genomic DNA.

Khorana, Kleppe and Molineaux recognized that hybridization and primer extension with a polymerase could be utilized to amplify nucleic acid (Kleppe K, Ohtsuka E, Kleppe R, Molineux I, Khorana H G, "Studies on polynucleotides. XCVI. Repair replications of short synthetic DNA's as catalyzed by DNA polymerases." *J Mol Biol* 56:341-61, 1971). Later, a thermostable polymerase, Taq DNA polymerase, was employed in this process, now known as PCR (Innis M A, Myambo K B, Gelfand D H, Brow M A, "DNA sequencing with *Thermus aquaticus* DNA polymerase and direct sequencing of polymerase chain reaction-amplified DNA." *Proc Natl Acad Sci USA* 85:9436-40, 1988). Taq polymerase is a thermostable enzyme which works efficiently at 70-75° C. The ability to catalyze DNA synthesis at elevated temperature makes Taq polymerase useful because this permits hybridization at higher temperatures, giving PCR greater specificity for the target to be amplified. Taq polymerase is also useful for sequencing templates which have extensive secondary structures at 37° C. (the standard temperature used for Klenow and Sequenase™ reactions).

Typically, in carrying out PCR one utilizes a high temperature (e.g., 95° C.) to separate the DNA and a lower temperature (e.g., 65° C.) to anneal and extend. In some cases, a different temperature is used for the extension, causing the reaction to require changing the temperature three times per cycle. The temperature changes are usually accomplished with a specialized device known as a "thermocycler" (commercially available from a number of companies, including F. Hoffmann-La Roche Ltd., Roche Molecular Systems, Inc., Nutley, N.J., USA and The Perkin-Elmer Corporation, Wellesely, Mass., USA). These devices are expensive and constrain the user to relatively large reaction volumes.

What is needed is a method for changing the temperature of reactions that is simple and inexpensive. Importantly, the method should be amenable to a variety of reaction types and reaction volumes.

SUMMARY OF THE INVENTION

Thus far, most devices that utilize Rayleigh-Bénard convection do so to allow for the increased dissipation of heat. See, for example, U.S. Pat. No. 6,515,857 ("Visual heat sink for computers and method of use") and U.S. Pat. No. 4,608,222 ("Method of achieving the controlled release of thermonuclear energy") to Ford, et al., and Brueckner, respectively. The utilization of Rayleigh-Bénard convection principles for conducting biological or biochemical reactions is a novel application. In order to use Rayleigh-Bénard convection for conducting biological or biochemical reactions it is necessary to provide a reaction chamber, reaction solutions, reaction starting molecules and a heat source (at or near the bottom of the reaction chamber). In some embodiments, a cooling source is also provided at or near the top of the reaction chamber. The length of the reaction (or total reaction time) can be limited by any applicable means. Some examples of methods to control the length of the reaction include rate limitation by depletion of starting molecules, accumulation of reaction end-products or by-products, change in temperature, addition of a termination substance(s) or change in pH.

In one embodiment, biological and biochemical reactions are performed in a Rayleigh-Bénard convection cell. The present invention is not limited to any particular reaction. Any reaction may be performed. In a preferred embodiment, reactions requiring temperature cycling may be performed. In a more preferred embodiment, polymerase chain reaction (PCR) is performed in a Rayleigh-Bénard convection cell. The present invention is not limited to the nature of the reaction performed in the reaction cell. Still, reactions that require thermocycling or that are not substantially hindered by thermocycling are ideally suited for execution in a Rayleigh-Bénard convection cell.

The reaction chamber may be made of any substance that does not interfere with or interact or interact adversely with the reaction constituents. In one embodiment, Plexiglas™ may be used by drilling or molding, for example, cylindrical chambers into the Plexiglas™. The size of the chamber and final shape will be determined by, for example, the volume of the reactants and the required temperature differential between the bottom and top of the chamber. In one embodiment, the reaction chamber for PCR is approximately 35 mL in volume and of approximately 1.5 cm in height (see, Examples, below). The chamber of the present invention is not limited to any particular size. In one embodiment, the reaction chamber has, for example, an aspect ratio (h/d, where h=height and d=diameter) of 3.3 and a Rayleigh-Bénard number (Ra) of $4.6 \times 10^5$. In another embodiment, the reaction chamber has, for example, a h/d ratio of 6.3 and an Ra of $3.7 \times 10^6$. One practiced in the art will be able to determine the necessary chamber size and confirmation based on the teachings of this specification and general knowledge in the art. In yet another embodiment, the reaction chamber is circular or oval (e.g., doughnut shaped with the doughnut standing on end, upright or vertically) with convection cycle traveling up one side of the circle (i.e., up one side of the doughnut) and down the other.

In other embodiments, other substances that may be used for the reaction chamber include, but are not limited to, glass, silicones, metals and plastics and other synthetic materials. In other embodiments, reaction chambers may be arranged in arrays such that numerous assays could be performed simultaneously. The present invention is not limited to any particular number of reaction chambers on an array or any particular arrangement of the reaction chambers. Arrays may comprise any number of reaction chambers. Arrays may also comprise multiple levels thereby allowing for stacking. In another embodiment, the invention comprises robotics. The use of robotics, e.g., for the loading of samples, removal of reactant products and monitoring of the reaction is contemplated by the present invention.

The present invention contemplates that the reaction chambers and arrays of the invention comprise, in one embodiment, heating elements, cooling means, probes, thermometers and other devices applicable to the particular reaction being performed. For example, in order to establish and maintain the heat convection of the present invention, it is contemplated that the reaction chamber or array is situated on a heating element such as, for example, a hot plate. In another embodiment, it is contemplated that the reaction chamber or array of the present invention comprises a heating element(s) directly attached to the chamber or array or built into the reaction chamber or array. In yet another embodiment, it is contemplated that the device comprises a receptacle that holds the reaction chamber(s) or array(s). In one embodiment, items such as heating elements, probes, thermometers, etc., are built into the device. An advantage of this design is that the reaction array(s) or reaction chamber(s) may be removed from the device, e.g., for the isolation of the reaction products contained in each reaction chamber. Additionally, the reaction chamber(s) or array(s) may be replaced as needed.

In another embodiment, the present invention comprises a cooling means (e.g., a water bath or refrigeration device). In another embodiment, the cooling means regulates the temperature of the top of the convection cell. It is contemplated that the convection cell may be cooled at the top with the cooling means or by transfer of the heat by convection into the surrounding environment. It is contemplated that the term "cooling" means maintaining the temperature at the top on the convection cell at a lower temperature than the bottom of the convection cell. The present invention is not limited by the means of achieving the temperature differential. For example, the top of the convection cell may be heated to a lesser extent than the bottom of the convection cell or the top of the convection cell may be cooled with a substance the is cooler than ambient temperature. In any case, the cooling substance may be a liquid or gas. In one non-limiting example, the liquid is water. In other non-limiting examples, the liquid is ethylene glycol, propylene glycol or blends of these chemicals with water. In another non-limiting example, the gas is ambient air. In yet another non-limiting example, the gas is a refrigerant such as freon (or, chlorofluorocarbons). In other non-limiting example, the gases used for cooling are ammonia, methyl chloride and sulfur dioxide.

The cooling means may also include a substance such as glass or metal (other non-limiting examples include ceramics and plastics) that is in contact or close proximity to the top surface of the solution located in the reaction vessel. The (for example) glass or metal can be cooled by passing the cooling substance (i.e., cooling liquid or cooling gas) over it or through it thereby lowing the temperature of the glass or metal. This, in turn, will regulate the temperature of the top surface of the liquid in the reaction vessel.

Cooling may be "active" and it may be "passive." "Active cooling" involves, for example, the use of a cooling device such as a water bath or refrigeration system. "Passive cooling" involves, for example, the release of heat into the ambient environment.

In one embodiment, the present invention contemplates that the temperature of the bottom of the convection cell (e.g., the temperature at the bottom of the reaction chamber or reaction vessel) is between 50-150° C., in a preferred embodiment between 90-100° C. and in a more preferred embodiment between 93-97° C. In another embodiment, the present invention contemplates that the temperature of the top of the convection cell (e.g., the temperature at the top of the reaction chamber or reaction vessel) is between 30-130° C., in a preferred embodiment between 50 and 70° C. and in a more preferred embodiment between 58-64° C. In yet another embodiment, the present invention contemplates that the temperature difference between the bottom and top of the convection cell is at least 5° C. In still yet another embodiment, the present invention contemplates that the temperature difference between the bottom and top of the convection cell is at least 10° C.

In one embodiment, the present invention contemplates a method, comprising: a) providing: i) a reaction vessel, ii) a heat source, iii) an active cooling means and iv) reactants; b) introducing said reactants to said reaction vessel to create a solution comprising a bottom solution surface and a top solution surface; and, c) applying heat to said bottom solution surface with said heat source and cooling said top solution surface with said active cooling means under such conditions that a temperature differential of at least 5° C. is established between said bottom solution surface and said top solution surface and a convection cell is established. In another embodiment, the present invention contemplates that the reactants comprise i) nucleic acid comprising a target and ii) primers substantially homologous to at least a portion of said target. In yet another embodiment, the present invention contemplates that reactant products are produced. In still yet another embodiment, the present invention contemplates that the products comprise amplified nucleic acid. In still yet another embodiment, the present invention contemplates that the reaction vessel comprises at least one material selected from the group consisting of Plexiglas™, glass, plastics, silicones and metal. In still yet another embodiment, the present invention contemplates that the reaction vessel is part of an array. In still yet another embodiment, the present invention contemplates that a temperature differential of at least 10° C. is established between said bottom solution surface and said top solution surface and a convection cell is established. In still yet another embodiment, the present invention contemplates at least one microdroplet channel wherein said microdroplet channel is in fluid communication with said reaction vessel.

In one embodiment, the present invention contemplates a system comprising i) a reaction vessel having a top and bottom suitable for establishing a convection cell with a temperature differential of at least 5° C. between the bottom of said vessel, ii) a heat source positioned at the bottom of said reaction vessel, iii) a cooling source positioned at the top of said reaction vessel and iv) a solution of biomolecules. In another embodiment, the present invention contemplates that the biomolecules are PCR primers. In still another embodiment, the present invention contemplates that the reaction vessel is comprised of material selected from a group consisting of Plexiglas™, glass, plastics, silicones and metal. In still yet another embodiment, the present invention contemplates that reaction vessel is part of an array. In still yet another embodiment, the present invention contemplates that the reaction vessel is in fluid communication with at least one microdroplet transport channel.

In one embodiment, the present invention contemplates a method, comprising: a) providing: i) a reaction vessel, ii) a heat source and iii) reactants; b) introducing said reactants to said reaction vessel to create a solution comprising a bottom solution surface and a top solution surface; and, c) applying heat to said bottom solution surface with said heat source and cooling said top solution surface by passive cooling under such conditions that a temperature differential of at least 5° C. is established between said bottom solution surface and said top solution surface and a convection cell is established. In another embodiment, the present invention contemplates that the reactants comprise i) nucleic acid comprising a target and ii) primers substantially homologous to at least a portion of said target. In yet another embodiment, the present invention contemplates that reactant products are produced. In still yet another embodiment, the present invention contemplates that the products comprise amplified nucleic acid. In still yet another embodiment, the present invention contemplates that the reaction vessel comprises material selected from the group consisting of Plexiglas™, glass, plastics, silicones and metal. In still yet another embodiment, the present invention contemplates that the reaction vessel is part of an array. In still yet another embodiment, the present invention contemplates that a temperature differential of at least 10° C. is established between said bottom solution surface and said top solution surface and a convection cell is established. In still yet another embodiment, the present invention contemplates that at least one microdroplet channel wherein said microdroplet channel is in fluid communication with said reaction vessel.

In one embodiment, the present invention contemplates a method, comprising: a) providing: i) a reaction vessel configured with a width between 1 mm and 3 mm and with a height of less than about 10 times said width, ii) a heat source, iii) a cooling means and, iv) reactants; b) introducing said reactants to said reaction vessel to create a solution comprising a bottom surface and a top surface; and, c) applying heat to said bottom solution surface with said heat source and cooling said top solution surface with said cooling means under such conditions that a temperature differential of at least 5° C. is established between said bottom solution surface and said top solution surface and a convection cell is established. In another embodiment, the present invention contemplates that the cross section the reaction vessel is without corners. In yet another embodiment, the present invention contemplates that the cross section the reaction vessel is with corners. In still yet another embodiment, the present invention contemplates that the reactants comprise i) nucleic acid comprising a target and ii) primers substantially homologous to at least a portion of said target. In still yet another embodiment, the present invention contemplates that reactant products are produced. In still yet another embodiment, the present invention contemplates that the products comprise amplified nucleic acid. In still yet another embodiment, the present invention contemplates that the reaction vessel comprises material selected from the group consisting of Plexiglas™, glass, plastics, silicones and metal. In still yet another embodiment, the present invention contemplates that the reaction vessel is part of an array. In still yet another embodiment, the present invention contemplates a temperature differential of at least 10° C. is established and a convection cell is established. In still yet another embodiment, the present invention contemplates at least one microdroplet channel wherein said microdroplet channel is in fluid communication with said reaction vessel.

DEFINITIONS

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule it, and like terms such as "polypeptide" or "protein," is not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid. The term "potion" when used in reference to a nucleic acid (as in "a portion of a given nucleic acid") refers to fragments of that nucleic acid. The fragments may range in size from ten bases to the entire nucleic acid sequence minus one base.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from ten nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe or primer that can hybridize to either or both strands of the double-stranded nucleic acid sequence under conditions of low to high stringency as described above.

The term "substantially homologous" when used in reference to a single-stranded nucleic acid sequence refers to any probe or primer that can hybridize the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, *in Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "detection assay" refers to an assay for detecting the presence or absence of a sequence or a variant nucleic acid sequence (e.g., a polymorphism in a given allele of a particular gene), or for detecting the presence or absence of a particular protein or the structure or activity or effect of a particular protein (e.g., a binding assay or activity assay) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. PCR is a method of nucleotide amplification.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" (PCR) refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter: PCR). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA.

Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter" or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue (e.g., muscle) in the relative absence of expression of the same nucleotide sequence of interest in a different type of tissue (e.g., bone, muscle, kidney, epithelium, etc.). Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic organism. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.).

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding mustang (e.g., SEQ ID NO:2) or fragments thereof may be employed as hybridization probes. In this case, the mustang encoding polynucleotide sequences are typically employed in an aqueous solution containing salts (e.g., NaCl), detergents (e.g., SDS), and other components (e.g., Denhardt's solution, dry milk, salmon sperm DNA, etc.).

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "array" shall be defined as an ordered arrangement of, for example, tubes or samples. The wells on a microtiter plate, for example, form an array. Arrays are usually two-dimensional but need not be. Arrays may also be three-dimensional. Arrays are useful, for example, in permitting the ordered analysis of a large number of samples.

The term "plastic(s)" shall be defines as a synthetic substance capable of being molded, formed or modeled.

The term "silicone(s)" shall be defined as any of a group of semi-inorganic polymers based on the structural unit $R_2SiO$, where R is an organic group, characterized by wide-range thermal stability, high lubricity, extreme water repellency, and physiological inertness and used in adhesives, lubricants, protective coatings, paints, electrical insulation, synthetic rubber, and prosthetic replacements for body parts.

The term "metal(s)" shall be defined as any of a category of electropositive elements that usually have a shiny surface, are generally good conductors of heat and electricity, and can be melted or fused, hammered into thin sheets, or drawn into wires. Typical metals form salts with nonmetals, basic oxides with oxygen, and alloys with one another. Additionally, metal(s) shall refer to an alloy of two or more metallic elements or an object comprising metal.

The term "convection cell" shall be defined as the (approximately) circulatory movement that occurs in a gas or fluid at a nonuniform temperature. While not limited to any particular mechanism, it is believed that the variation of the density of the fluid or gas and the action of gravity generates the movement. In one embodiment, a convection cell is generated by applying a heat source to the fluid, e.g., at or near the bottom of the fluid.

The term "heat source" shall be defined as a device that generates heat, preferably, in a controlled manner so that the heat output may be regulated. An example of a heat source for the present invention is an electrical resistor. A resistor is defined as an element included in an electrical circuit to provide resistance to the flow of current.

The term "reactants" shall be defined as a substances (e.g., chemicals) taking part in a chemical reaction. In a PCR reaction, for example, some of the reactants are targets, proteins, nucleotides (dNTPs) and polymerases. "Reactant products" are substances that result after two or more reactants undergo a reaction.

The term "Rayleigh-Bénard convection" or "convection cell" shall be defined as, in brief, a convection in which packets (i.e., continuous areas within the total volume) of fluid move primarily in vertical directions based on temperature gradients and gravity. A more complete explanation of the Rayleigh-Bénard convection is given in the General Description of the Invention, infra.

The term "biomolecules" shall be defined as any organic molecule that is an essential part of a living organism. Nucleic acids, amino acids, lipids and carbohydrates are non-limiting examples of biomolecules.

The term "cooling" is a relative term and it means, for example, maintaining temperature at the top on the convection cell at a lower temperature than the bottom of the convection cell. The present invention is not limited by the cooling means. In fact, heat may be used in the "cooling" of the top of the convection cell as long as the temperature of the top of the convection cell is maintained at a temperature lower than the bottom of the convection cell. It is not necessary that the top or bottom of the convection cell maintain an exact temperature as long as the reaction being run in the convection cell can progress. Also, cooling may be "active" and it may be "passive." "Active cooling" involves, for example, the use of a cooling device such as a water bath or refrigeration system. "Passive cooling" involves, for example, the release of heat into the ambient environment.

The term "in fluid communication" shall be defined as having a fluid linking two or more items together or having a channel (for example) through which fluid can flow. For example, in the present invention, one embodiment contemplates microchannels that are in fluid communication with the convection cell of the present invention.

The term "bottom solution surface" shall be defined as the solution near or at the bottom of a vessel (e.g., a reaction vessel). In one embodiment, the bottom solution surface comprises no more than (and preferably less than) about 50% of the volume of the total solution. In a preferred embodiment, the "bottom solution surface" comprises no more than (and preferably less than) about 25% of the total volume of the solution (e.g., about 10% or less).

The term "top solution surface" shall be defined as the solution near or at the top of a vessel (e.g., a reaction vessel). In one embodiment, the solution comprises no more than (and preferably less than) about 50% of the volume of the total solution. In a preferred embodiment, the "top solution surface" comprises no more than (and preferably less than) about 25% of the total volume of the solution.

The terms "circular," "cylindrical" and "vessel without corners" shall be defined, in regards to embodiments of a reaction vessel of the present invention, as a vessel that when viewed in cross section is without corners. A circular vessel is not necessarily perfectly round. For example, oblong and elliptical vessels are also contemplated as being defined by this term. Additionally, the vessel need not be symmetrical. The cross section of the vessel may, for example, be egg shaped.

The terms "rectangular," "square" and "vessel with corners" shall be defined, in regards to embodiment of a reaction vessel of the present invention, as vessel that when viewed in cross section is with corners. In this regard, the term rectangular includes, for example, squares, trapezoids, parallelograms. Additionally, the term refers to vessel shapes with less than four or more than four corners such as triangles and pentagons.

"Channels" are pathways through a medium (e.g., silicon, glass, plastic, metal) that allow for movement of liquids and gasses. Channels thus can connect other components, i.e., keep components "in liquid communication." "Microdroplet transport channels" or "microchannels" are channels configured (in microns) so as to accommodate "microdroplets." While it is not intended that the present invention be limited by precise dimensions of the channels or precise volumes for microdroplets, illustrative ranges for channels and microdroplets are as follows: the channels can be between 0.35 and 50 µm in depth (preferably 20 µm) and between 50 and 1000 µm in width (preferably 500 µm), and the volume of the microdroplets can range (calculated from their lengths) between approximately one (1) and (100) nanoliters (more typically between ten and fifty).

BRIEF DESCRIPTION OF FIGURES

FIGS. 7(A-C) show theoretical estimation of the inlet liquid pressure from the curvature of the liquid drop.

GENERAL DESCRIPTION OF THE INVENTION

I. Rayleigh-Bénard Convection

The present invention is not limited to any particular theory. In fact, it is not necessary to have an understanding of the underlying theory to perform the invention. All the same, a review of the underlying theories of Rayleigh-Bénard convection are provided.

The partial differential equation(s) that describe convective flow analytically have been studied for the past 200 years, with rewarding results, but the exact analytical solutions of these are yet to be found. Still, even though convective flow has not been completely dissected theoretically, the physical parameters that control the process are known. The nature of the theoretical difficulties can be understood well if we realize that even a simple system undergoing convective energy interaction requires a complete knowledge of the fluid mechanics and heat transfer involved in the process.

Physically, a fluid layer heated from below, a supposedly simple system of convective interaction, experiences forces that drive the convective flow resulting from the buoyancy of the heated layer. The magnitude of such forces vary depending on the temperature difference prevailing between the top and bottom portion of the fluid layer. The complexity is enhanced further since the temperature distribution is affected to a large extent by the convective flow itself, which carries heat from the bottom to the relatively colder top portion of the fluid. In other words, the driving force which causes the flow itself is driven to modifications by the flow.

Earliest description of convection was written in the 1790's by Benjamin Thompson, Count Rumford, which he used to account for the transfer of heat in an apple pie. Only in the 1900's were the systematic investigations undertaken. The most significant and pertinent experimental work was carried out by the Frenchman Henri Bénard. He studied a seemingly simple convective system which he never knew was so complicated that the real physics behind it was uncovered only recently. In the 1900's convection was taken as one of the myriad things that John William Strutt, Lord Rayleigh, studied in his illustrious and prolific carrier. In one of his last articles, published in 1916, he attempted to explain what is now known as Rayleigh-Bénard Convection. Though his explanation has been superseded in later years, his work remains as the starting point for most of the modern theories of convection.

Rayleigh's Theory

Figure 5:
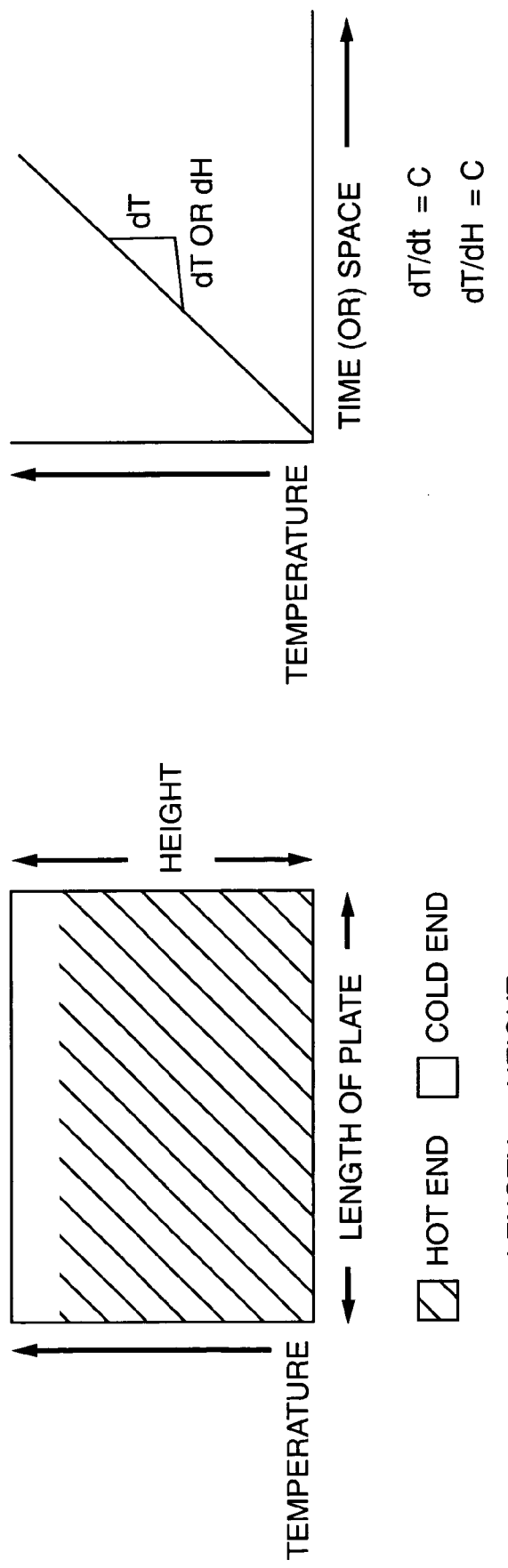
FIG. 5 shows temperature distributions in a convection cell.

A fluid with simplified properties, as opposed to a real one, is used in a two dimensional model to help explain convection (see, FIG. 5). A thin layer of the fluid is confined fully between two semi-infinite (small, definite thickness vertically and long, infinite length horizontally as shown in the adjacent figure) flat plates so that there is no gap (free surface). A "thin layer" is defined to mean that the horizontal dimension of the fluid layer is very large when compared to that of the vertical. This arrangement ensures that the interference of the side boundaries (walls, etc.) is kept to a minimum. The fluid is heated from the bottom in such a way that the temperature of the bottom portion of the fluid remains relatively uniform (spatial invariance) and steady (temporal invariance). Similarly it is assumed that the top portion also behaves in the same fashion so that the temperature gradient across the height also is uniform. This means, in other words, that a graph of Temperature vs. Time is a straight line (as shown). Other theoretical assumptions are as follows; it is assumed that the fluid itself is:

1. Incompressible—which is valid as the layer is of very small dimensions;
2. The density of the fluid is the only property that gets affected by the change in the temperature across it;
3. It experiences uniform gravitational force on the entire volume.

In this model, consider a packet of fluid in a convection cell. The study of the forces which affect the fluid packet's motion can lead us to a better understanding of the mechanism involved. The packet considered can be of any size and shape but the displacement should be small. The initial displacement of the packet need not be due to any imbalance in the forces in the convection cell. Rather, the forces result from a random displacement from the mean position. This will eventually occur given enough time. For understanding what is happening in the model one has to be familiar with some basic concepts: buoyancy, viscosity, surface tension and thermal diffusivity of fluids (see, below).

Buoyancy

CASE 1: Without heating, buoyancy effects will be due to the pressure difference across the fluid packet which when balanced by the weight force of the packet. This ensures static equilibrium.

CASE 2: With heating, the fluid packet has lesser density at the bottom relative to the surrounding medium which makes it rise because the increase in buoyancy force disrupts the static equilibrium.

Figure 1:
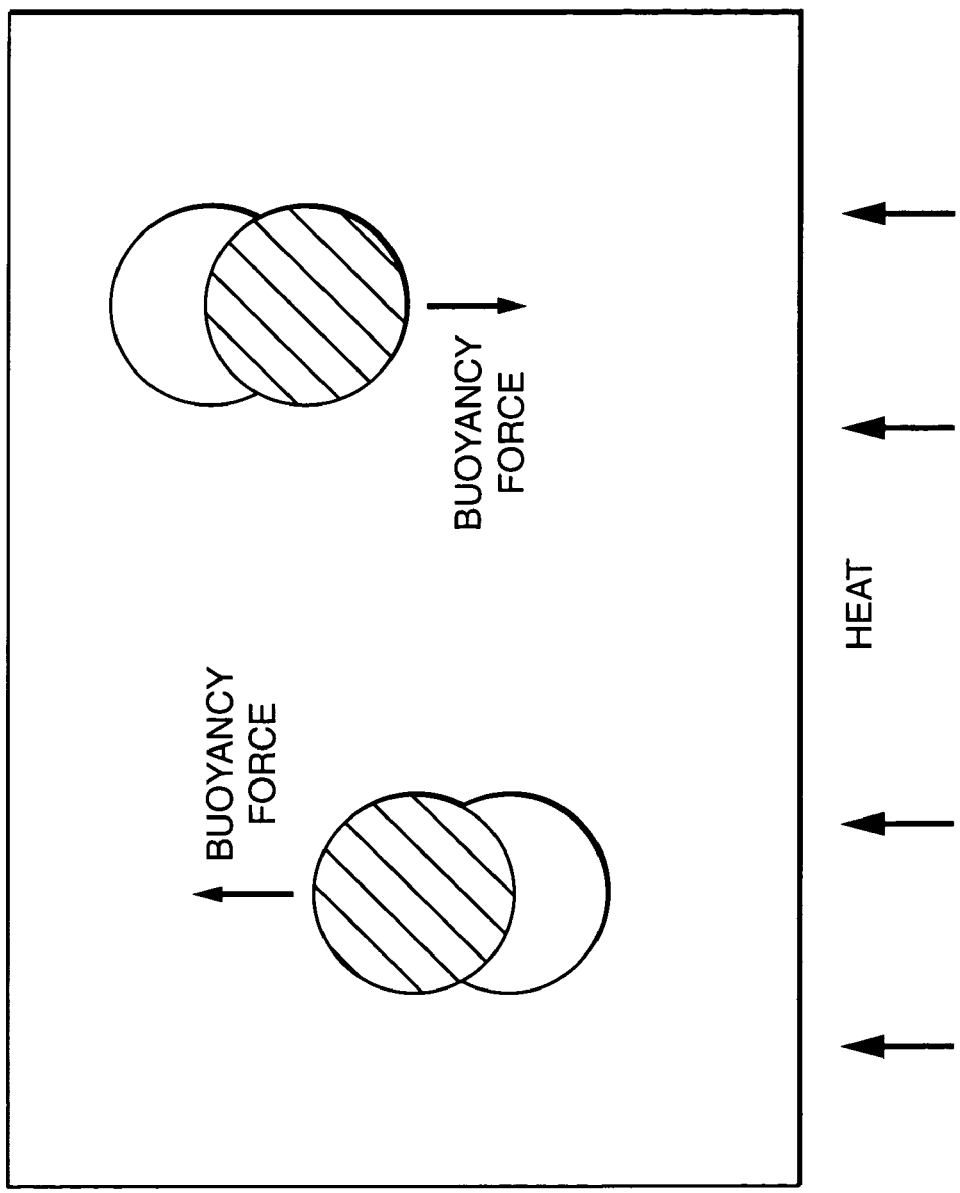
FIG. 1 shows the effect of heat on buoyancy force.
Figure 2:
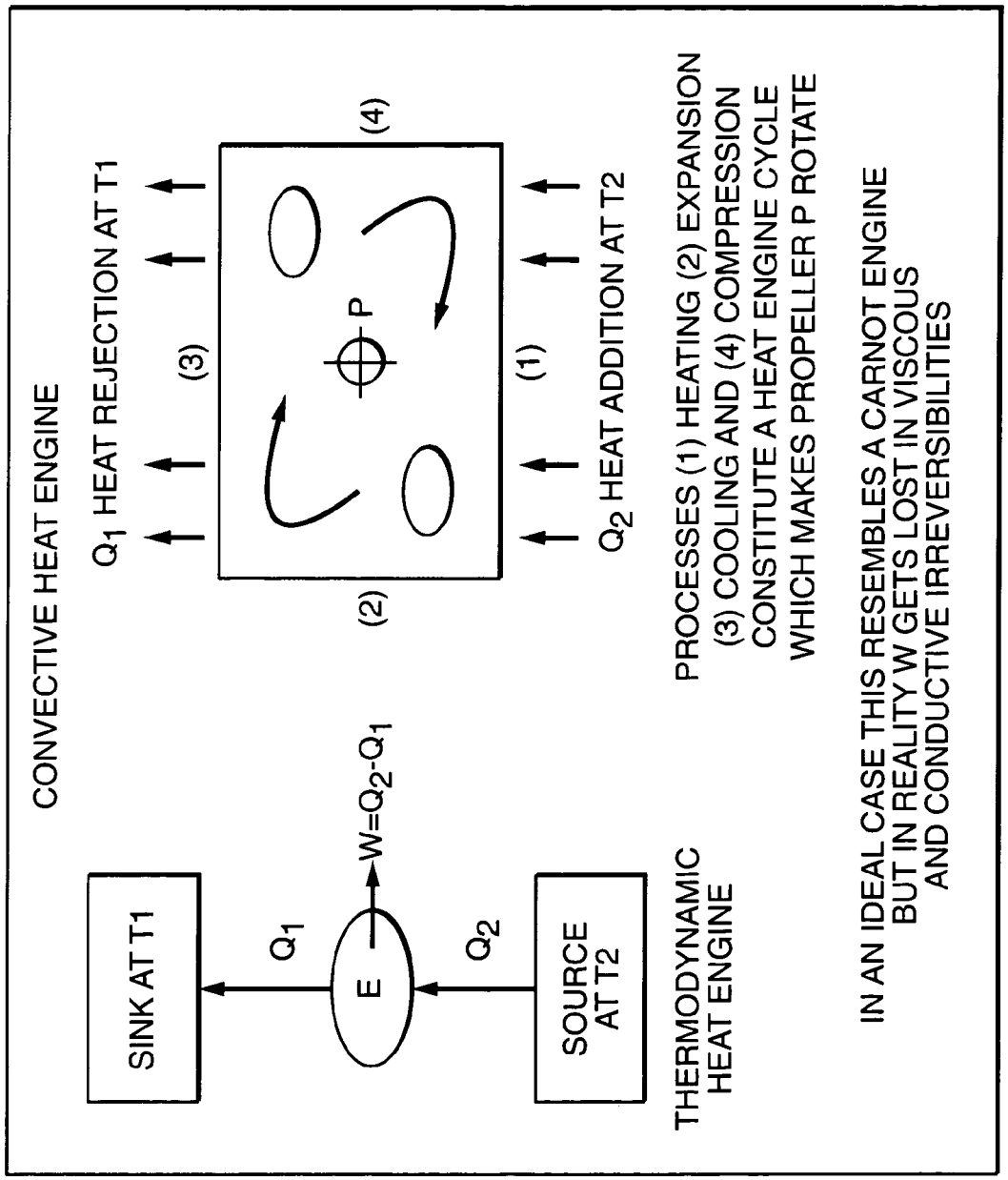
FIG. 2 shows a diagram of convective flow field.

In FIG. 1, the convection cell holding the fluid packet is filled with, for example, water. With out the addition of any other force, it will stay in the position inside the trough maintaining its static equilibrium. This is because the weight of the packet is balanced by 1) the upward reaction force and 2) the water in the trough. This is called the buoyancy force. The pressure in the water trough increases as we go down because the weight of the water layer above each point also contributes to the net force experienced by that point. So, this static pressure is greater on the bottom side of the packet than at the upper surface. This balance in forces can get affected by the actual weight of the fluid in the packet and the pressure difference across the packet. For a heavier packet, the weight force increases causing the packet to sink to a different height where the upward buoyancy force equals the weight force to make the packet float. So, heavier objects of identical volume hence but with higher density sink as compared to lighter, less dense objects.

Now, consider the same fluid packet at the bottom of the trough in the earlier figure but with heat supplied to it from below, as shown. This packet will have a higher temperature and, therefore, a lesser density when compared to the average density of the entire layer. Once at the top of the convection chamber and away from the heat source, the fluid packet will lose heat. Thus a fluid packet at the top of the convection cell will have relatively higher density than the surrounding medium due to its lesser temperature. In the bottom side, as long as the fluid packet remains in its position, it is surrounded by fluid of identical average density and so maintains its static equilibrium with the surrounding. Suppose now, due to some random fluctuation, a displacement is given to the packet in the upward direction. This will result in an imbalance in the forces acting on the packet.

To explain this in another way, the fluid packet which was originally of lesser density than the surrounding average density due to its higher temperature now will be pushed up into a region of higher density. This will create a positive buoyancy which causes the packet to raise. The raise will be sustained till the fluid packet rises to a level where it's density equals that of the surrounding. At this point it will simply float as the static equilibrium is restored. The upward force is proportional to the density difference and volume of the packet. As the fluid packet raises through regions of relatively colder fluid whose average density progressively increases due to the lack of additional heat, it results in an increased density gradient between the packet and the surrounding which accelerates the raise.

On similar analysis, the downward push of a packet of fluid makes it enter a region of lesser average density resulting in the 'heaviness' of the packet thus propelling it down. Thus, the whole of the fluid layer is eventually overturned resulting in a circulation of the fluid between the hot and cold ends.

It seems from this analysis that convection will be observed in a fluid region whenever there is a temperature gradient, however small it may be. But such sensitive dependence of the initiation of the flow on the temperature gradient is not observed in actual circumstances. There seems to be a cut-off value, of some variable which governs the phenomenon, beyond which only convective flow results. This value was explained by Lord Rayleigh.

Rayleigh Number and its Physical Significance

The onset of convection has to take into consideration two more modes of energy dissipation in the fluid. In other words, the force imbalance equation which explains the convective motion has to be recast to accommodate two more forces. One of our initial assumptions is that before the temperature gradient prevails, the fluid is at rest and is not subjected to any external influence which might induce motion. So, when the fluid tries to move, or circulate, it does so with minimum velocity. When the fluid packet moves, its motion is impeded by the 'viscous drag' between it and the surrounding fluid.

Viscosity, as we know, is internal fluid resistance. It is given by the formula $$t=m\ du/dy$$

where t=the shear stress applied, m=the dynamic viscosity and du/dy=the change in the velocity component in a perpendicular direction. It is like a frictional force acting in the opposite direction of motion. In the fluid packet, this acts against the buoyancy force and tries to impede motion. If the magnitude of the viscous drag force equals the buoyancy force, motion will cease.

The second dissipative effect is from the fact that convection is not the only mode of heat transfer that could happen in the given circumstance. Conduction and radiation are the other two. Radiative effects are predominant only at very large temperature values and can usually be safely ignored. However, conductive transfer cannot be ignored. In a real non-adiabatic situation, the fluid packet is displaced into a cooler surrounding due to the buoyancy force. This immediately causes the packet to diffuse out the heat energy to the surrounding fluid because a temperature difference exists between the fluid packet and the surrounding medium.

The fundamental definition of heat states that the molecules in the warm packet can not have a higher average velocity than that of the surrounding medium. This allows the molecules in the packet to move more freely thereby exchanging energy with the surrounding molecules of lesser velocity resulting in the equalization of velocities. This results in the packet cooling more rapidly than one may logically expect. The rapid cooling of the fluid packet (as compared to the surrounding medium) initiates the downward travel of the fluid packet. For a downward moving fluid packet (moving from a cooler environment to a warmer environment) the heat transfer is in the other way causing the fluid packet to warm more quickly that the surrounding medium.

So, if the local temperature difference is reduced by heat diffusion, it results in a reduction in the buoyancy force. It is necessary that the buoyancy force, which is the result of the temperature gradient, must exceed the dissipative forces of viscous drag and heat diffusion to ensure the onset of convective flow. The gravitational potential energy given out by the displacement of the fluid packet up and down must be more than the 'fluid brake' and 'heat diffusion.' To better realize the influence of these forces on the onset of convection, these forces are expressed as a non-dimensional number called the Rayleigh Number (Ra). The Rayleigh Number is the buoyant force divided by the product of the viscous drag and the rate of heat diffusion:

$$Ra=gbDTL^3/an$$

where b is the coefficient of thermal expansion; DT the temperature difference between hot and cold end; L the width (vertical distance between the walls); a the thermal diffusivity and n the kinematic viscosity of the fluid. Convection sets in when the Rayleigh Number exceeds a certain critical value. Thus, the Rayleigh Number is a quantitative measure or representation of when the 'switch' from conductive to convective transport happens for a given configuration (henceforth, the dominant energy transport mechanism would be convection).

Modifications of Rayleigh Theory

Lord Rayleigh's analysis of the problem of convective flow was initiated by the experiments of Bénard. While trying to explain those experiments, Rayleigh devised the theory explained above. This theory, unfortunately, assumes a model experiment which is in a subtle way different from the actual experiments of Bénard. So this theory fails in explaining those experiments.

The experimental conditions Bénard employed were different in the sense that the fluid layer was not fully confined between two horizontal rigid plates, as assumed in the model above, but was open to air at the upper surface. Since the surface is open, surface tension forces can affect the flow. These forces can affect and even dominate over convective flow and the buoyancy force.

The predictions of the Rayleigh Theory would be in error for the experiments and a successful alternate theory was introduced in 1958 by J. R. A. Pearson of the Imperial College of Science & Technology in London. A new dimensionless number called the Marangoni Number, named after the 19th century Italian investigator, includes the effects of surface tension on convective flow and was introduced by Pearson to explain the experiments of Bénard.

As a result, the Rayleigh Theory has been accepted to explain buoyancy-induced convective flows while the newly introduced theories have been accepted to explain the Bénard convection. The Rayleigh Theory and other theories modeled on it explain the conditions required for the onset of convective flow but fail to explain what happens once the flow is initiated.

Stability Analysis

As convection is motion due to force imbalance, it is often convenient to analyze it in terms of stability. This analysis is given in FIG. 4.

Figure 4:
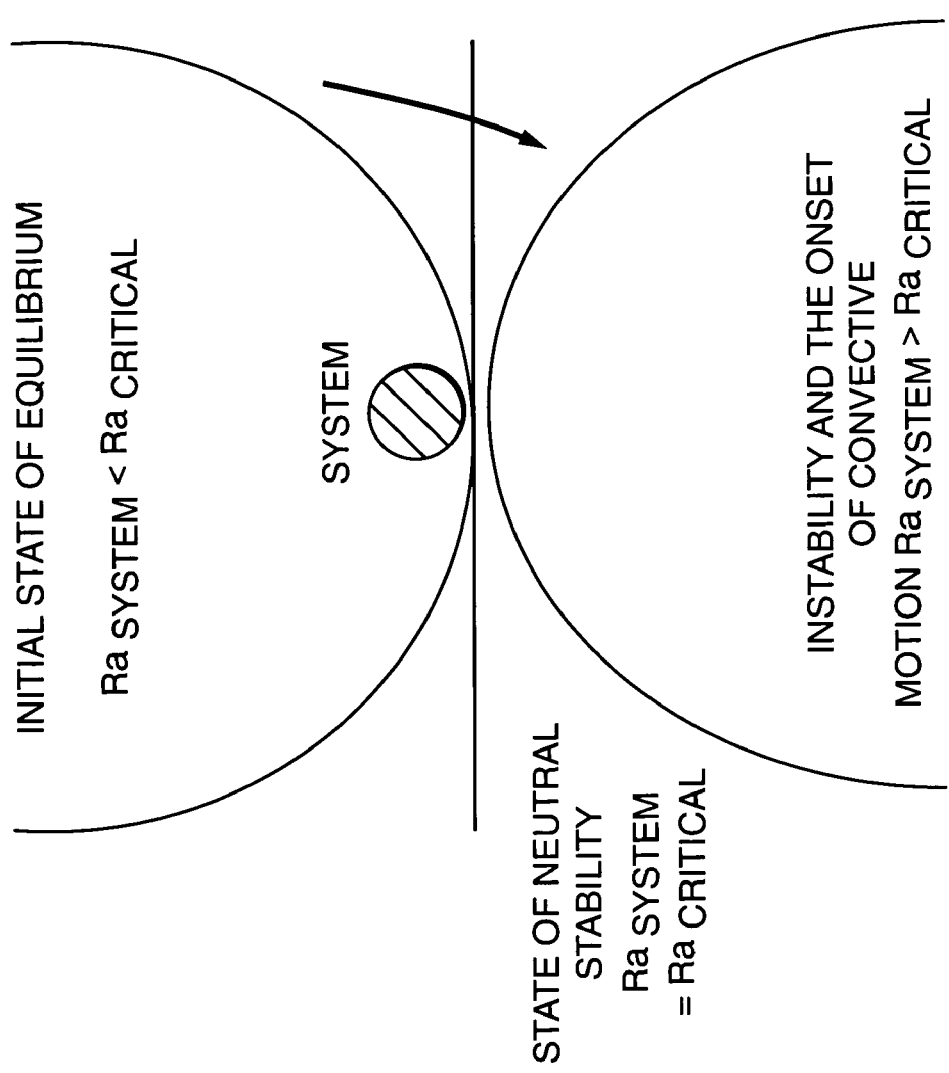
FIG. 4 shows a schematic diagram of the state of neutral stability achieved in a convection flow cell.

Let's assume that a system is usually found at the minimum energy state. This is represented in FIG. 4 as the circle at the lowest point in the bowl. As the Rayleigh Number increases, this lowest point of maximum stability will be converted to the top and, therefore, to a point of maximum instability of the system. This results in the onset of convective motion. This is illustrated in FIG. 4 as the 'bowl' inverting. (In FIG. 4, the arrow indicates that the 'bowl' has inverted). Because of the inversion of the bowl, the 'marble' is no longer stable and can now move. Of course, in a convection cell, the movement of the fluid packet would be upwards and not downwards as the illustration indicates. From this analysis, it can be predicted that for a particular value of Rayleigh Number the potential surface will be a straight line of neutral stability. Above that number, convective instability (and, therefore, convective flow or motion) will begin.

The Rayleigh Theory of the onset of convective motion in a fluid layer enclosed between two plates, though having many simplifying assumptions, nevertheless, successfully explains the conditions required for the initiation of convection in real fluids. But, even the more comprehensive theories of later years cannot explain all the observed features of a fully developed convective flow in enclosed spaces. Only qualitative descriptions are possible.

Convection Cells

Figure 3:
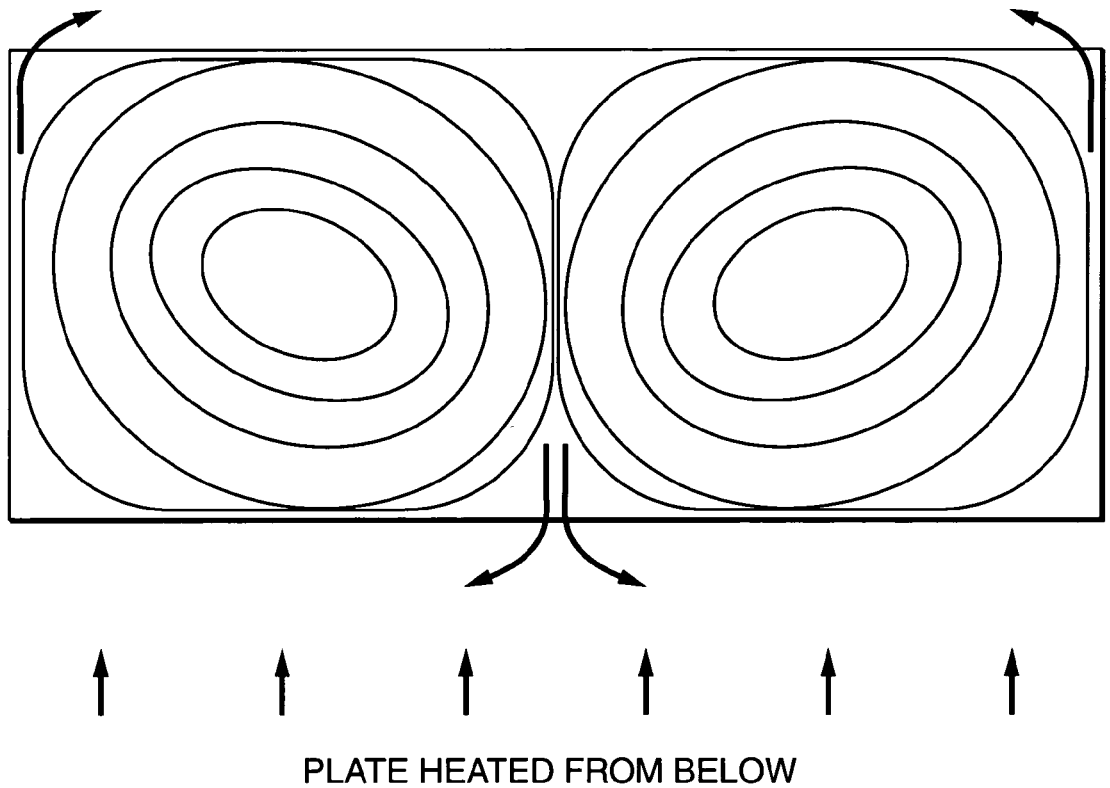
FIG. 3 shows a schematic diagram of a Rayleigh-Benard convection cell.

When the critical Rayleigh Number is exceeded and as instability sets in, the hot layer tries to go up simultaneously when the cold upper layer tries to come down. Both things will not happen at the same time and the fluid avoids this stalemate by separating itself into a pattern of convective cells. In each cell, the fluid rotates in a closed orbit and the direction of rotation alternates with successive cells. This roll, when viewed in cross section, resembles a square or rectangle where the height is being determined by the width of the fluid layer. FIG. 3 shows an example of the cells in the two-dimensional view.

The Convective Engine

A free convective flow is, thermodynamically, a heat engine. In other words, it is a contrivance which by energy interaction with two external heat reservoirs gives useful work output. The descriptions below relate to FIG. 3.

1. Here, the fluid packet is composed of mass dm. The movement of this packet is initiated because it receives heat energy at the bottom of the chamber from a heat source causing it to expand. In effect, it receives heat energy and undergoes an isothermal expansion process.
2. With this energy the volume increases forcing an imbalance that results in the initial upward movement of the fluid packet. The upward movement results in further expansion as the packet raises. This results in an adiabatic expansion process in which the packet moving up can perform some work.
3. As the fluid packet goes up the packet loses the remaining heat energy to the surrounding medium to maintain equilibrium. This is an isothermal compression process. The fluid packet cools and contracts as it progresses to the top of the chamber. (In some instances the cooling is via convection; in other instances a cooling means is employed).
4. Finally the cooled fluid packet circulates back to the bottom. This happens through an adiabatic compression process; as the packet further contracts as it comes down.

In short, the fluid packet of mass dm executes a cycle comprising heating-expansion-cooling-compression. The processes executed by the fluid packet are the processes that constitute a Carnot Heat Engine Cycle.

II. Polymerase Chain Reaction

The polymerase chain reaction is a test tube system for DNA replication that allows a "target" DNA sequence to be selectively amplified, or enriched, several million-fold in just a few hours. Within a dividing cell, DNA replication involves a series of enzyme-mediated reactions, whose end result is a faithful copy of the entire genome. Within a test tube, PCR uses just one indispensable enzyme—DNA polymerase—to amplify a specific fraction of the genome. PCR is described in U.S. Pat. Nos. 4,683,195, 4,683,202, and 4,965,188 to Mullis, which are incorporated herein by reference.

PCR is a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

A more complete description of PCR follows. During cellular DNA replication, enzymes first unwind and denature the DNA double helix into single strands. Then, RNA polymerase synthesizes a short stretch of RNA complementary to one of the DNA strands at the start site of replication. This DNA/RNA heteroduplex acts as a "priming site" for the attachment of the DNA polymerase, which then produces the complementary DNA strand. During PCR, high temperature is used to separate the DNA molecules into single strands, and synthetic sequences of single-stranded DNA (20-30 nucleotides) serve as primers. Two different primer sequences are used to bracket the target region to be amplified. One primer is complementary to one DNA strand at the beginning of the target region; a second primer is complementary to a sequence on the opposite DNA strand at the end of the target region.

To perform a PCR reaction, a small quantity of the target DNA is added to a test tube with a buffered solution containing DNA polymerase, oligonucleotide primers, the four deoxynucleotide building blocks of DNA, and the cofactor $MgCl_2$. The PCR mixture is taken through replication cycles consisting of:

1. One to several minutes at 94-96 degrees ° C., during which the DNA is denatured into single strands;
2. One to several minutes at 50-65 degrees ° C., during which the primers hybridize or "anneal" (by way of hydrogen bonds) to their complementary sequences on either side of the target sequence; and
3. One to several minutes at 72 degrees ° C., during which the polymerase binds and extends a complementary DNA strand from each primer.

As amplification proceeds, the DNA sequence between the primers doubles after each cycle. Following thirty such cycles, a theoretical amplification factor of one billion is attained.

Two important innovations were responsible for automating PCR. First, a heat-stable DNA polymerase was isolated from the bacterium *Thermus aquaticus*, which inhabits hot springs. This enzyme, called the Taq polymerase, remains active despite repeated heating during many cycles of amplification. Second, DNA thermal cyclers were invented that use a computer to control the repetitive temperature changes required for PCR.

Following amplification, the PCR products are usually loaded into wells of an agarose gel and electrophoresed. Since PCR amplifications can generate microgram quantities of product, amplified fragments can be visualized easily following staining with a chemical stain such as ethidium bromide. While such amplifications are impressive, the important point to remember is that the amplification is selective—only the DNA sequence located between the primers is amplified exponentially. The rest of the DNA in the genome is not amplified and remains invisible in the gel.

Following the introduction of PCR, the technique spread through the community of molecular biologists like—well, a chain reaction. As more scientists became familiar with PCR, they introduced modifications of their own and put the technique to new uses. Almost overnight, PCR became a standard research technique and the practical applications soon followed.

PCR has many functions in, for example, biotechnology, medical research and in medical diagnosis. Not surprisingly, the first applications to leave the laboratory dealt with the detection of genetic mutations. In this regard, PCR has proven a quick, reliable method for detecting all manner of mutations associated with genetic disease—from insertions, to deletions, to point mutations.

PCR can also be used to detect the presence of unwanted genetic material, as in the case of a bacterial or viral infection. Conventional tests that involve the culture of microorganisms or use of antibodies can take weeks to complete or be tedious to perform. PCR offers a fast and simple alternative. For example, in the diagnosis of AIDS, PCR can be used to detect the small percentage of cells infected by the human immunodeficiency virus (HIV). DNA isolated from peripheral blood cells is added to a PCR reaction containing primers complementary to DNA sequences specific to HIV. Following amplification and gel electrophoresis, the presence of an appropriate-sized PCR product indicates the presence of HIV sequence and therefore, HIV infection.

The sensitivity of PCR is so great that signals may be obtained from degraded DNA samples and sometimes from individual cells. This ability and the inherent stability of DNA have combined to permit DNA to be amplified from some unusual sources, such as an extinct mammal called the quaga, an Egyptian mummy, and a three-million-year-old termite trapped in amber. This situation has, almost overnight, transformed ignored museum collections of biological specimens into treasure troves of genetic information. Evolutionary biologists are using these specimens and PCR to explore the genetic relatedness of organisms across species boundaries and now even across time.

When PCR is used with degraded DNA samples, it can synthesize an amplification product, even if the sample's average fragment size is less than the distance between the primer binding sites. During PCR, overlapping fragments within the target sequence can function as primers to generate full-length amplification products. This ability of PCR to utilize degraded DNA samples is of great interest to forensic scientists who must sometimes work with human cells in very poor condition. The technique has provided conclusive identifications in cases where conventional DNA typing has failed. Ironically, the greatest concern about the widespread use of PCR in forensic medicine is the technique's extreme sensitivity. Even minuscule amounts of DNA left over from previous amplifications can be reamplified, leading to an inconclusive result.

The present invention will greatly aid in the facilitation of these and other uses of PCR by permitting the large-scale application of PCR to more diverse sample populations.

DESCRIPTION OF THE INVENTION AND PREFERRED EMBODIMENTS

The present invention relates to microfabrication and biological reactions in microfabricated devices, and in particular, the performance of reactions in Rayleigh-Benard convection cells. Since the use of such devices may be supplemented by the addition of ancillary devices and control mechanisms (for example, for the movement of solutions and reagents to and from the convection cells), the description of the invention includes I) the design of microscale devices (comprising microdroplet transport channels, reaction chambers, electrophoresis ports, and radiation detectors) using silicone and glass substrates, II) the creation (or definition) of microdroplets having a discrete size, III) movement of discrete microdroplets using a surface-tension-gradient mechanism in which discrete microdroplets are differentially heated and propelled through etched channels, IV) flow control with sealed valves, V) mixing of biological samples for reactions, VI) microliter and nanoliter liquid metering and, VII) microfabrication of ancillary devices.

I. Design of MicroScale Devices

Although there are many formats, materials, and size scales for constructing integrated convection cell systems, the present invention contemplates Plexiglas™ and silicone microfabricated devices as a cost-effective solution. Plexiglas™ is a well known, easily workable and easily available material. Silicone is the material used for the construction of computing microprocessors and its fabrication technologies have developed at an unprecedented pace over the past 30 years. While this technology was initially applied to making microelectronic devices, the same techniques are currently being used for micromechanical systems.

Rayleigh-Bénard convection flow is a well know principle used in heat transfer (see, e.g., Zhang, P., et al., "Patterns in spherical Rayleigh-Benard convection: a giant spiral roll and its dislocations" *Phys Rev E Stat Nonlin Soft Matter Phys* 66(5 Pt 2):055203, 2002). However, the application of Rayleigh-Bénard convection flow has not been made to biochemical and biological reactions; especially those reactions that are facilitated by thermocycling. Typically, such reactions are performed by either transferring the reaction constituents from one vessel to another or by altering the temperature of the entire contents of the vessel. Application of Rayleigh-Bénard convection flow principles to biological and biochemical reactions will allow for the efficient performance of reactions without the necessity of transferring small volumes of liquid or continually regulating and changing the temperature of the reaction vessel. The design of the reaction device need not be complicated. The device may consist of a sheet of solid material into which reaction chambers are drilled or molded. In a preferred embodiment, the chambers are cylindrical. A heating device is used at the bottom of the chamber to initiate and maintain the Rayleigh-Bénard convection flow. The heating device is preferably external to the chamber. It may be integral with the chamber material (e.g., molded into the chamber material) or it may be external to the chamber material (e.g., a heating plate on to which the chamber material may be placed).

As a mechanical building material, Plexglas™ and silicone have well-known fabrication characteristics. The micromachining techniques are, essentially (but not limited to), drilling, molding and laser cutting. The economic attraction of silicone devices is that their associated micromachining technologies are, essentially, photographic reproduction techniques. In these processes, transparent templates or masks containing opaque designs are used to photodefine objects on the surface of the silicone substrate. In both cases the patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost provided that all of the components are compatible with the silicone micromachining process. While other substrates, such as glass or quartz, can use photolithographic methods to construct microfabricated analysis devices, only Plexglas™ and silicone give the added advantage of allowing a large variety of electronic components to be fabricated within the same structure.

In silicone micromachining, a simple technique to form closed channels or chambers involves etching an open trough or well on the surface of a substrate To create a channel, a second, unetched substrate can be bonded over the open channel. There are a wide variety of isotropic and anisotropic etch reagents, either liquid or gaseous, that can produce channels or chambers with well-defined side walls and uniform etch depths. When producing channels, since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures. Additionally, chambers can be produced by terminating the etching process early to prevent the formation of holes that completely pass through the surface but, rather, pass a prescribed distance into the material being etched.

II. Microfluid Dynamics

The devices and method of the present invention may be combined with devices and methods for the manipulation of microvolumes of fluid. As such, this application incorporates by reference U.S. Pat. Nos. 5,626,764, 6,048,734, 6,057,149, 6,130,098, 6,271,021, 6,379,929 to Burns, et al.

In this regard, and as detailed in the above referenced patents, the present invention contemplates, for example, methods, compositions and devices for the creation of microdroplets of discrete (i.e. controlled and predetermined) size and for the movement of those microdroplets. In one embodiment, the present invention contemplates the use of selective hydrophobic coatings to develop a liquid-sample injection and motion system that does not require the use of valves. In one embodiment, the present invention contemplates a method of lift-off to pattern hydrophobic and hydrophilic regions on glass, quartz and silicone substrates, involving i) the deposition of a hydrophobic reagent (such as a self-assembled monolayer film of OTS) on a silicon oxide surface patterned by a metal layer and ii) subsequent removal of the metal to give hydrophobic patterns. Other substrates such as plastics can also be used after depositing a think film of silicon oxide or spin-on-glass.

Previous work in patterning hydrophobic surfaces have been done by photocleaving of such monolayer films. The photocleaving procedure uses Deep-UV exposure to make the molecules of the monolayer hydrophilic. By contrast, the present invention contemplates a method which eliminates the use of high-power UV source; rather the preferred method of the present invention uses simple microfabrication procedures.

Following the proper hydrophobic patterning of the surface (e.g., the surface of a microdroplet transport channel), the present invention contemplates the placement of a patterned etched glass cap over the pattern on a flat surface. The hydrophobic/hydrophilic channels thus formed can then be used to move precise nanoliter-volume liquid samples.

In one embodiment, the present invention contemplates the compositions and methods are suitable for devices having a variety of designs and dimensions, including, but not limited to, devices with chamber volumes from, for example, 0.24 mm$^3$ to 10.0 mm$^3$ and for channel dimensions of, for example, 40 µm by 500 µm. Drop splitting and motion is seen with 1-3 seconds using voltages between 4.5 volts to 7.5 volts (the resistance of the heaters varied between 9.5 ohms to 11 ohms). The size of the drop split is between approximately 25 and approximately 50 nanoliters, depending on the value "L" used for the channel design. Keeping the heaters actuated keeps the microdroplet moving almost to the end of the channel (a distance of around 12.5 mm); the time taken depends on the voltage applied to the heater and the volume of the chamber. Initiation of drop motion is seen sooner for the operation of devices with smaller chambers. While an understanding of precise mechanisms is not needed for the successful practice of the present invention, it is believed that with smaller chamber, the volume is smaller and higher values of pressure are achieved more quickly. The maximum temperatures reached near the heater are approximately 70° C. measured by the RTD.

III. Movement of Discrete MicroDroplets

The present invention describes and, in some embodiments, includes the controlled movement of liquid samples in discrete droplets in silicone. Discrete droplet transport involves a system using enclosed channels or tubes to transport the liquid to the desired locations. Within the channels, discrete liquid reagent microdroplets can be injected, measured, and moved between the biochemical analysis components. Discrete droplet movement has three advantages. First, each sample droplet is separated from all others so that the risk of contamination is reduced. Second, in a uniform channel, the volume of each sample can be determined by merely measuring the droplet length. Third, the motion of these droplets can be accomplished with simple heating (i.e., using internal forces and no moving parts). Movement is performed using thermal gradients to change the interfacial tension at the front or back of the droplets and, thus, generate pressure differences across the droplet. For example, a droplet in a hydrophilic channel can be propelled forward by heating the back interface. The local increase in temperature reduces the surface tension on the back surface of the droplet and, therefore, decreases the interfacial pressure difference. The decreased pressure difference corresponds to an increase in the local internal pressure on that end of the droplet ($P_1$ increases). The two droplet interfaces are no longer in equilibrium, with $P_1$ greater than $P_2$, and the pressure difference propels the droplet forward.

That is to say, forward motion can be maintained by continuing to heat the droplet at the rear surface with successive heaters along the channel, while heating the front surface can be used to reverse the motion of the droplet. Applying a voltage to the wire beneath the channel generates heat under the edge of the droplet. Heating the left interface increases the internal pressure on that end of the droplet and forces the entire droplet to the right. The pressure on the interior of the droplet can be calculated knowing the atmospheric pressure, $P_{atm}$, the surface tension, a, and the dimensions of the channel. For a circular cross-section, the interior pressure, $P_i$, is given by $P_i=P_{atm}-(4\sigma \cos \theta)/d$ where d is the diameter of the channel and θ is the contact angle. Since σ is a function of temperature ($\sigma=\sigma_o(1-bT)$ where $\sigma_o$ and b are positive constants and T is the temperature), increasing the temperature on the left end of the droplet decreases the surface tension and, therefore, increases the internal pressure on that end. The pressure difference between the two ends then pushes the droplet towards the direction of lower pressure (i.e., towards the right). The aqueous droplet shown is in a hydrophilic channel (0<θ<90); for a hydrophobic channel (90<θ<180), heating the right edge would make the droplet move to the right.

Contact angle hysteresis (the contact angle on the advancing edge of the droplet is larger than the contact angle on the retreating edge) requires a minimum temperature difference before movement will occur. The velocity of the droplet after motion begins can be approximated using the equation $v=ÆPd^2/32 \mu L$ where $ÆP$ is the pressure difference, µ is the viscosity of the solution, and L is the length of the droplet. The present invention contemplates temperature differences of greater than thirty (30) degrees Centigrade to create movement. Experiments using temperature sensors arrayed along the entire channel indicate that a differential of approximately 40° C. across the droplet is sufficient to provide motion. In these experiments, the channel cross-section was 20 µm×500 µm, and the volume of each of these droplets can be calculated from their lengths and is approximately 100 nanoliters for a 1 cm long droplet.

IV. Flow Control with Sealed Valves

The present invention contemplates the use of sealed valves to control fluid flow. While the present invention is not limited to a particular sealing method, in one embodiment, an actuating force pushes a diaphragm against a valve seat to restrict fluid flow and the diaphragm is then sealed to the valve seat. In such an embodiment, the solder pads are associated with a heating element that can melt the solder. This liquified solder flows over areas of the valve seat and diaphragm to cover contamination, cracks and crooks between the diaphragm and valve seat. With the actuating force still holding the diaphragm and valve-seat together, the heating element is turned off to allow the solder to cool and re-solidify. Upon solidification, the actuating force can be released and the valve is sealed. To open the valve again, the solder can be liquified without applying an actuation force.

In a preferred embodiment, the valve is designed such that solder pads are placed on the diaphragm or valve seat. While the present invention is not limited to a precise method of placing these solder pads, it is specifically contemplated that they can be electroplated.

V. Mixing Biological Samples in Reactions

Droplet motion (described generally above) is contemplated as one step in a pathway. The other steps typically involve sample mixing and a controlled reaction. For example, the integral heaters arrayed along the entire surface of the channel used for droplet motion also allow for a region of a channel to be used as a thermal reaction chamber. For sample mixing prior to the reaction, a Y-channel device is contemplated. In such a device, a first droplet containing a first sample (e.g., nucleic acid) is moved along one channel of the Y-channel device, and a second droplet containing a second sample (e.g., a restriction digest enzyme in digestion buffer) is moved along the other channel of the Y-channel device.

Following sample merging, there is the concern that the combined samples have not been properly mixed. That is to say, if two similar microdroplets enter the single channel in laminar flow at the same flow rate, they will form an axially uniform droplet but will not be mixed width-wise. Width-mixing can be accomplished in a number of ways.

First, there is simple diffusion, although, for large DNA molecules, the characteristic time for this mixing could be on the order of several hours or more. Circulation patterns generated inside the droplets during movement and heating significantly reduce this time. In this regard, the present invention contemplates maintaining the mixture as a heated mixture (e.g., maintaining the temperature at 65° C. for 10 minutes) using the integral heaters and temperature sensors.

Second, the present invention contemplates mixing by reversing the flow direction of the mixture over a relatively short distance in the channel. While a variety of reverse flow approaches are possible, one or two direction changes over a distance comprising approximately two droplet lengths has been found to be adequate.

Finally, there is the mixing approach wherein the mixture is moved against or over physical obstacles. For example, the mixture can be either "crashed" back against merge point of the Y-channel or simply moved over deliberate imperfections in the channel (i.e., "roller coaster" mixing).

Successful mixing, of course, can be confirmed by characterization of the product(s) from the reaction. Where product is detected, mixing has been at least partially successful. The present invention contemplates, in one embodiment, using electrophoresis to confirm product formation.

VI. Microliter and Nanoliter Liquid Metering

In some embodiments of the present invention, it may be necessary to meter microliter and nanoliter-sized drops. In that regard, the first step involved, prior to manipulating and controlling discrete drops inside a microchannel network, is the injection and metering of microliter and nanoliter-sized discrete drops. As such, it is crucial for the success of a variety of miniaturized chemical analysis systems. The ability to meter microliter and nanoliter-sized drops not only minimizes the usage of samples and reagents, but also reduces the total size of the complete analytical system. In some embodiments, precision in on-chip metering is also necessary in order to quantify the subsequent sample preparation (e.g., mixing, reaction) steps as well as to compare between experiments performed in different devices.

Figure 6A:
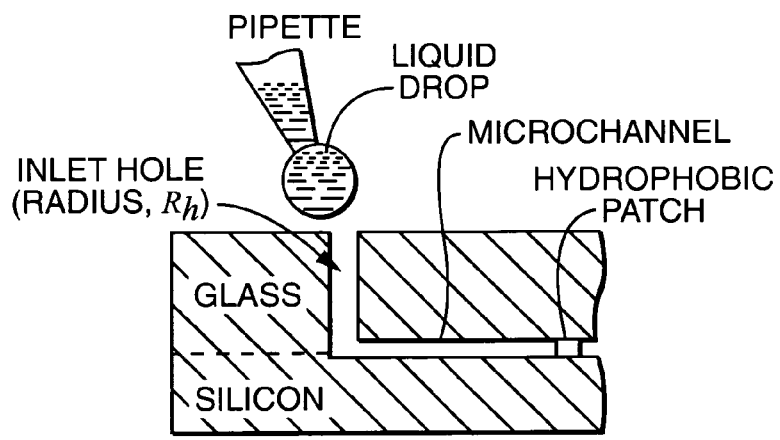
FIGS. 6(A-C) illustrate stopping liquid at a hydrophobic patch inside a microchannel. (A & B) shows a schematic of the procedure. (C) shows micrographs of the actual mechanism.
Figure 6B:
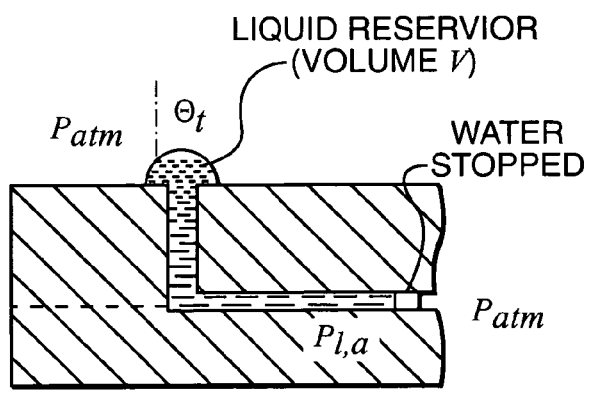
Figure 6C:
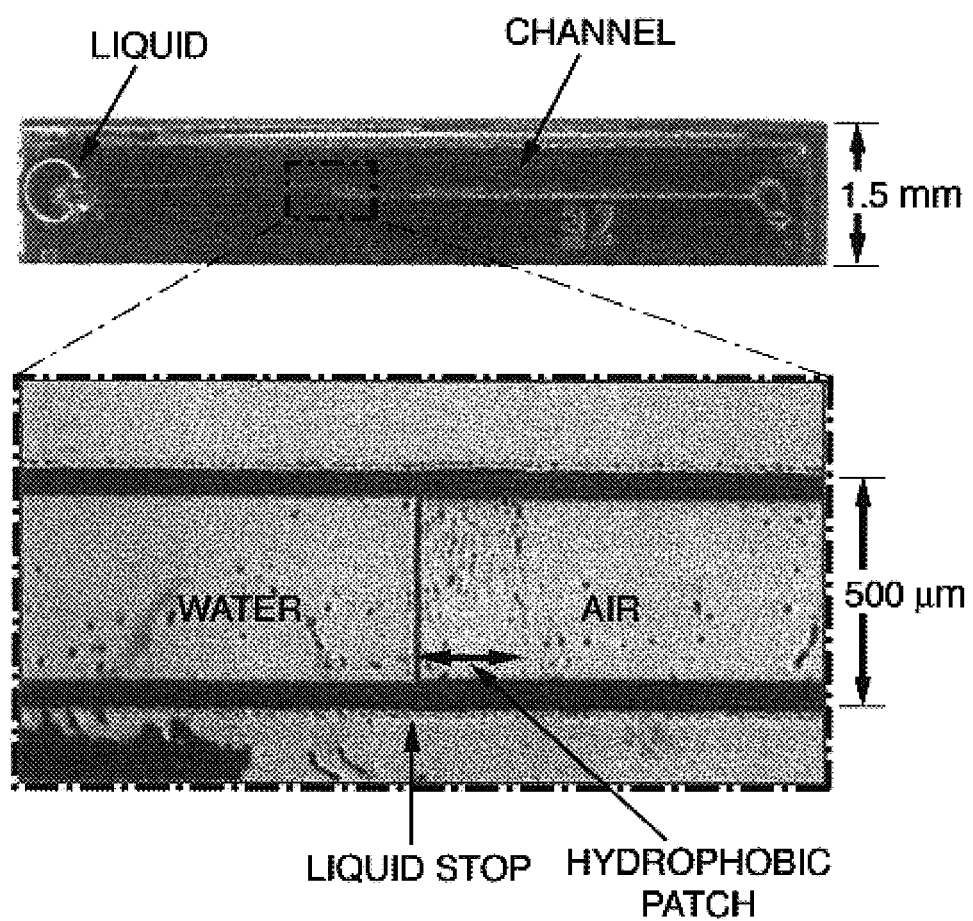

FIGS. 6(A-C) presents a liquid drop (~μl) placed at the inlet hole using a pipette (FIG. 6A). The liquid is drawn inside the microchannel by capillary forces and is stopped at the hydrophobic patch (FIG. 6B). (FIG. 6C) Photograph of a microchannel (100 μm×20 μm) device showing liquid being stopped at the hydrophobic patch (200 μm wide). The ability of a hydrophobic patch to stop liquid inside a microchannel (FIGS. 6A-C) can be ascertained by studying the net pressure acting on the liquid inside the microchannel after the advancing liquid front has reached the hydrophobic patch (FIG. 6B). A positive pressure difference is required for additional liquid to flow from the inlet hole over the hydrophobic patch. In order for the hydrophobic patch to stop the flow of liquid from the reservoir, the pressure difference, ignoring gravity effects, must be equal to or less than zero:

$$\Delta P = P_{l,i} - P_{l,a} \leq 0 \tag{1}$$

In the above expression, $P_{l,i}$ is the pressure in the liquid reservoir and $P_{l,a}$ is the pressure in the liquid side when the advancing liquid front reaches the hydrophobic patch. These pressures can be calculated in order to design a device that will successfully control the fluid position. Note that the height of liquid in the inlet hole is of the order of a millimeter and pressure due to liquid height is negligible ($\phi gh \sim 1000$ kg/m$^3 \times 9.8$ m/s$^2 \times 1$ mm$\sim 10$ N/m$^2$ only).

The internal liquid pressures are not equal to atmospheric pressure due to surface tension forces but the pressures can be calculated knowing the radius of curvature of the liquid-air interfaces ($R_c$) and the surface tension of the liquid ($\sigma$).

As illustrated by FIG. 7A, a liquid drop placed at the inlet assumes a section of a sphere (radius $R_v$) with base radius $R_b$ and height h. The liquid-air interface experiences a contact angle of $\theta_t$. As show in FIG. 7B, once $R_b = R_h$, the interface gets pinned at the periphery of the hole and the base radius remains constant. As illustrated by FIG. 7B, the pressure difference across the liquid-air interface at the inlet is estimated using Laplace's equation for water ($\sigma = 72$ mN/m) for different drop volumes. The pressure inside the excess liquid drop ($P_{l,i}$) at the inlet hole (FIG. 7A) is higher than atmospheric pressure. The difference in pressure can be calculated using Laplace's equation and is given by the following relationship. Adamson, A. W., *Physical Chemistry of Surfaces*, 5th ed., Wiley, New York, 1990, 395-399:

$$P_{lj} - P_{atm} = \frac{2\sigma}{R_c}. \tag{2}$$

The mean radius of curvature of a given volume of liquid (V) can be calculated knowing the shape of the drop. Surface tension works to minimize the surface area and create a spherical segment whereas gravity tends to flatten the drop. For drop volumes of the order of 1 μl, the surface tension forces are more than an order of magnitude higher than gravity forces. The liquid drop therefore assumes the shape of a spherical segment (Radius, $R_v$). The two principal radii of curvatures of the liquid surface are both equal to the radius of the sphericular segment, $R_v$ and therefore the mean radius of curvature is given by:

$$R_c = R_c \tag{3}$$

The radius of the liquid drop ($R_v$) can be calculated from the volume of the liquid drop (V) and the contact angle $\theta_t$ experienced by the liquid on the top of the device (FIG. 7A). $R_v$ is given as:

$$R_v = \left[ \frac{6V}{\pi(1-\cos\theta_t)^2(4-\cos\theta_t-3\cos^2\theta_t)} \right]^{\frac{1}{3}} \tag{4}$$

Note that Equation (4) holds for any value of contact angle $\theta_t$ but only if the liquid extends past the inlet hole (i.e., $R_b > R_h$). Once $R_b = R_h$ (FIG. 13b), $R_v$ can be calculated from the hole radius ($R_h$) and liquid height h as:

$$R_v = \frac{R_h^2 + h^2}{2h}. \quad (5)$$

The liquid height can be calculated from the following expression involving liquid volume and the hole radius:

$$h^3 + 3R_h^2 h - \frac{6V}{\pi} = 0 \quad (6)$$

Using Equations (2) through (6), the pressure difference across the liquid-air interface at the inlet hole can be calculated and plotted as a function of drop volumes (V) for different top contact angles and a constant hole radius (FIG. 7C). The increase in interfacial pressure with a decrease in the volume of liquid is due to the decrease in $R_c$ as a function of volume. However, once $R_b=R_h$, further decreasing V results in an increase in $R_c$, and therefore, a decrease in pressure. The rise in interfacial pressure for $R_b > R_h$ is very prominent for drop volumes less than 0.05 μl (see insert in FIG. 7C). Note that as the contact angle increases from 0° to 180°, the radius of curvature decreases and, therefore, the liquid pressure increases.

Figure 8A:
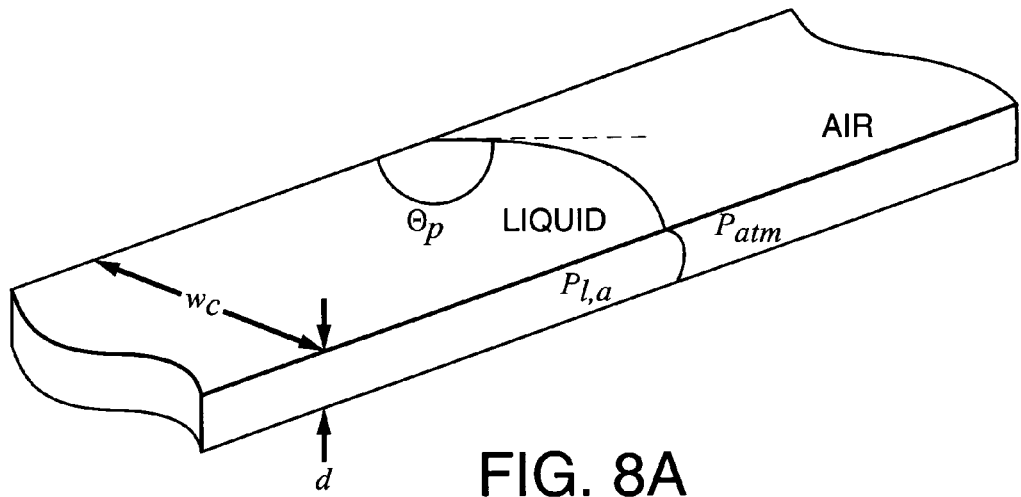
FIGS. 8(A and B) show a theoretical estimation of the liquid pressure at the hydrophobic patch in a microchannel.
Figure 8B:
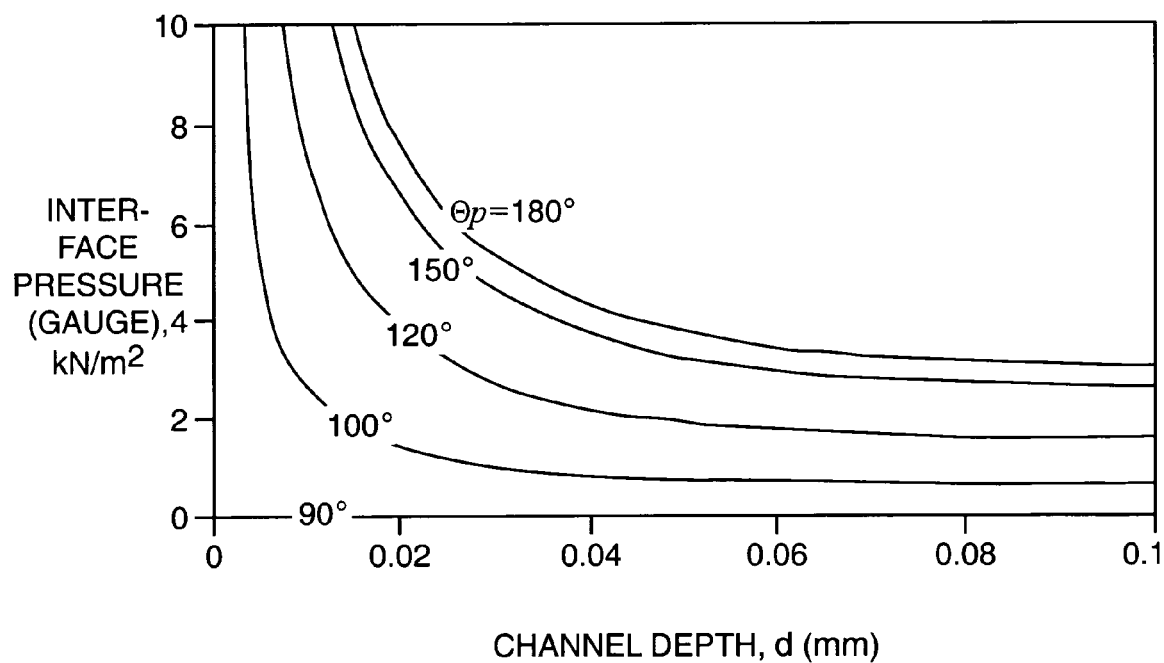

The interface pressure of the liquid front advancing into the capillary ($P_{l,a}$) can also be determined. FIG. 8A demonstrates the liquid-air interface inside the rectangular capillary is a bent cylinder which maintains a constant contact angle of $\theta_p$ at all the walls. FIG. 8B presents the pressure difference across the liquid-air interface is calculated using Laplace's equation for water (σ=72 mN/m) for different slit-type microchannels, varying in the depth. The interface pressure of the liquid front advancing into the capillary ($P_{l,a}$) can also be determined. The curved surface is such that a constant contact angle $\theta_p$ is maintained at the wall of the channel (FIG. 8A). For a rectangular capillary, we have the following relation for the mean radius of curvature. Kim, E.; Whitesides, G. M. *J Phys. Chem. B*, 1997, 101, 855:

$$R_c = \left[\cos\theta_p\left(\frac{1}{w_c} + \frac{1}{d}\right)\right]^{-1}. \quad (7)$$

In the above expression, $w_c$ is the width and d is the depth of the microchannel. Using Equation (7) and a relationship similar to Equation (2), the interfacial pressure difference can be calculated for different channel cross-sections and contact angles. The liquid pressure is given by the following relationship:

$$P_{l,a} = P_{atm} - 2\sigma\cos\theta_p\left(\frac{1}{w_c} + \frac{1}{d}\right). \quad (8)$$

The microchannels used in this study have depths of 20-60 μm and widths of 100-500 μm. At these dimensions, the interface pressure is strongly dependent on the channel depth, as shown in FIG. 14b, and increases with decreasing channel depths. Moreover, the pressure increases with an increase in the contact angle.

As stated earlier, $P_{l,i} - P_{l,a} \leq 0$ in order to stop the liquid sample at the hydrophobic patch:

$$\left[\frac{\pi(1-\cos\theta_t)^2(4-\cos\theta_t-3\cos^2\theta_t)}{6V}\right]^{\frac{1}{3}} + \frac{\cos\theta_p}{d} \leq 0 \quad (9)$$

Note that the above expression is obtained using equations (1)-(4) and (8) and holds for the base radius of the liquid volume being larger than the inlet hole radius ($R_b > R_h$) and (d<<$w_c$). From Equation (9), we can see the channel depth must be sized for the liquid volume placed at the inlet and for the hydrophobic contact angle of the patch and the top surface of the device.

Figure 9:
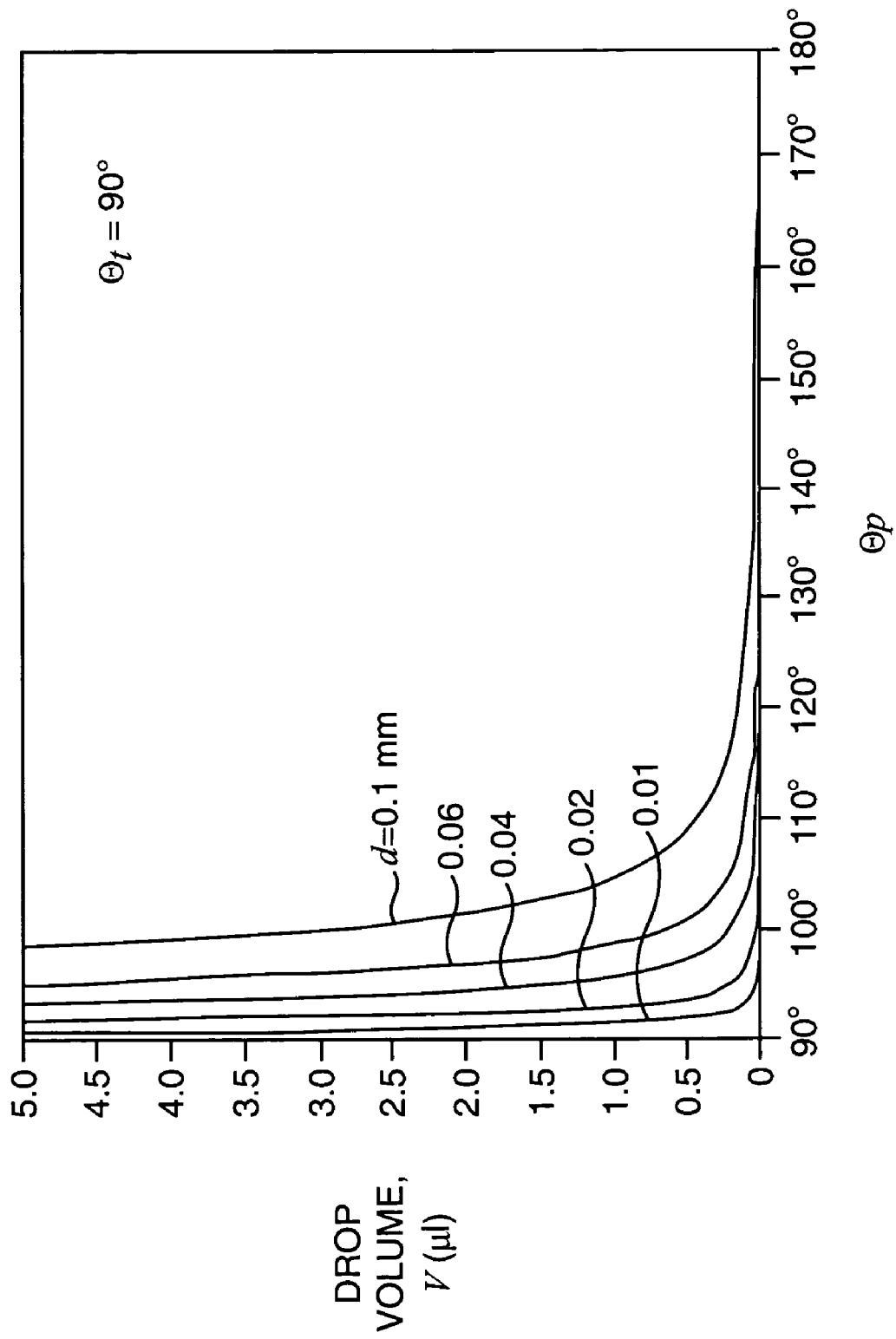
FIG. 9 defines liquid stopping criterion at the hydrophobic patch.

FIG. 9 presents plots where the inlet pressure is balanced by the pressure at the hydrophobic patch. In order for liquid to be stopped at the patch (contact angle $\theta_p$), the liquid volume should be higher than that on the plot for a given channel depth. FIG. 9 also plots lines of $P_{l,i}-P_{l,a}=0$ for different channel depths and a top contact angle ($\theta_t$) of 90°. For a given patch contact angle ($\theta_p$), there exists a threshold drop volume which lies on the ($P_{l,i}-P_{l,a}=0$) lines for different channel depths. The liquid volume should be higher than the threshold amount for the hydrophobic patch to stop liquid. Mechanical pipetters, used routinely in laboratories can pipette drops as small as a microliter with an accuracy of half a microliter. For such drop volumes (few μl), a contact angle of 100° is high enough to stop liquid in microchannels with depths below 60 μm, as observed in experiments (FIGS. 6A-C) and predicted by theory (FIG. 9).

Figures 10A, 10B:
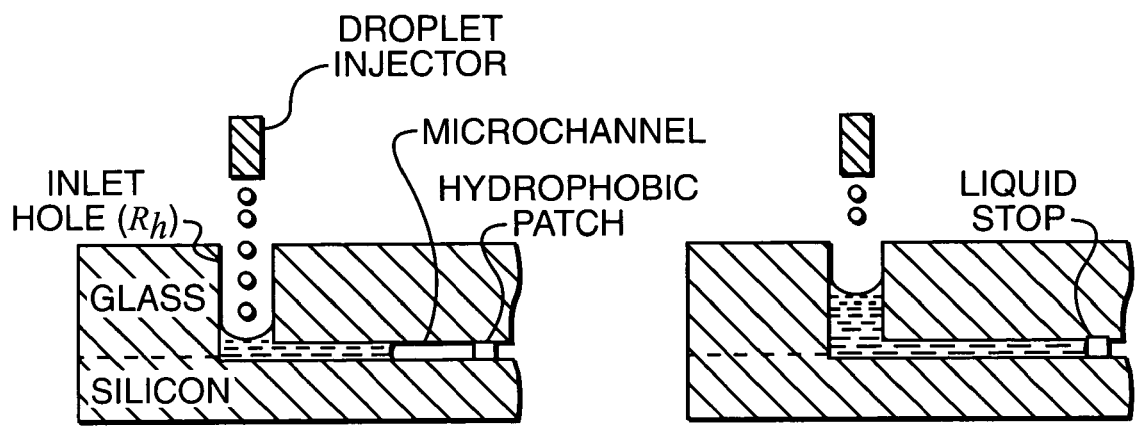
FIGS. 10(A-D) illustrate liquid introduction by piezoelectric droplet dispensing.
Figures 10C, 10D:
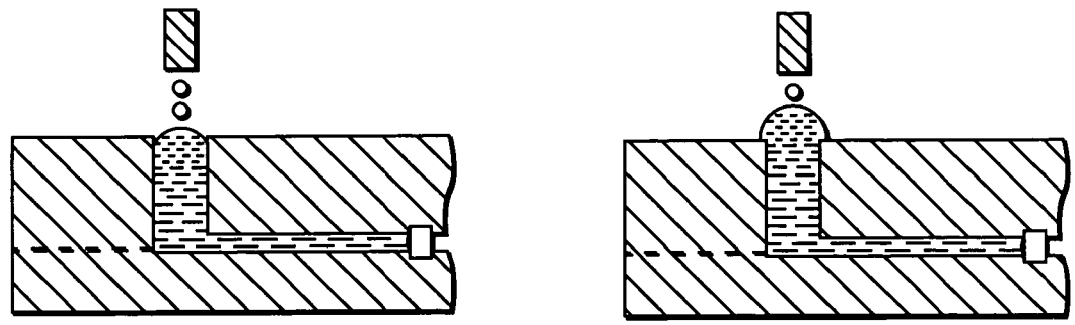

In the above discussions, we have described liquid being introduced into microchannels by placing excess liquid on the microchannel device. An alternative way of introducing liquid is presented in FIG. 10 wherein liquid starts filling in the microchannel up to the hydrophobic patch and then rises in the inlet hole (FIGS. 10B-C) until it overflows out of the inlet hole (FIG. 10D). Another method is to inject minute droplets in succession into the microchannel (FIG. 10A) using piezoelectric or other aerosol-type dispensers. The droplet dispensing may be stopped either (a) when the inlet hole begins to fill (FIG. 10B), (b) when the inlet hole is full (FIG. 10C), or after excess liquid has spilled out of the inlet hole (FIG. 10D).

The first two ways of filling of the microchannel (FIGS. 10B and C) will always ensure that the liquid preferentially moves into the smaller channel due to capillary action and stop at the hydrophobic patch ($\theta_p > 90°$). However, once the liquid overflows out of the inlet hole (FIG. 10D), the liquid pressure at the inlet may become more than atmospheric and will oppose the liquid pressure at the hydrophobic patch. The liquid pressure at the inlet depends on the inlet hole radius (see Equations (2), (3) and (5)) and therefore the inlet hole may be designed to ensure liquid is stopped at the hydrophobic patch for all three ways of microchannel filling (FIG. 10B-D).

As discussed earlier, the ability of a hydrophobic patch to stop liquid at a hydrophobic patch can be determined by studying the net pressure acting on the liquid (Equation (1)). The liquid pressure at the inlet can be evaluated using Equations (2), (3), (5) and (6), the maximum value of which is obtained when (h=$R_h$):

$$(P_{l,i})_{max} = P_{atm} + \frac{2\sigma}{R_h} \quad (10)$$

The liquid pressure at the hydrophobic patch can be evaluated as before, using Equation (8).

In order to satisfy the condition $P_{l,i} - P_{l,a} \leq 0$ for liquid to stop at the patch, we have the following relationship:

$$\frac{1}{R_h} + \frac{\cos\theta_p}{d} \leq 0 \quad (11)$$

Note that we have assumed the channel depth to be small compared to the channel width (i.e. $d \ll w_c$) while deriving the inequality given in (11). Therefore, the inlet hole may be sized in order to stop liquid in a channel for the hydrophobic contact angle of the patch. The inlet hole has to be made larger than the threshold hole radius ($=d/\cos\theta_p$) in order to stop liquid at the patch. Note as the hydrophobic contact angle increases, the threshold hole radius decreases. Increasing the channel depth also increases the threshold radius.

Liquid Splitting Using Air Pressure

Figure 11A:
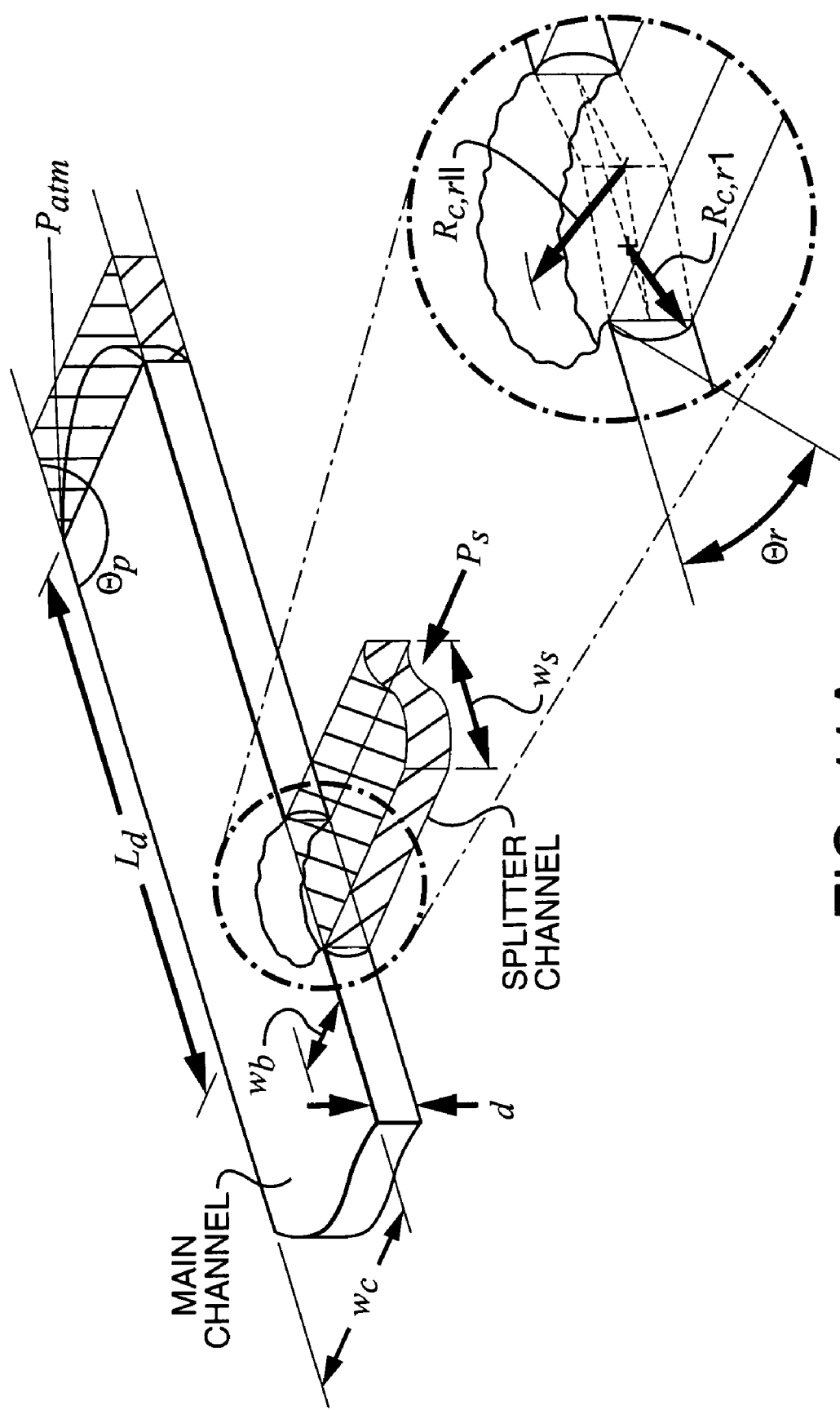
FIGS. 11(A & B) show a theoretical estimation of liquid splitting pressures.
Figure 11B:
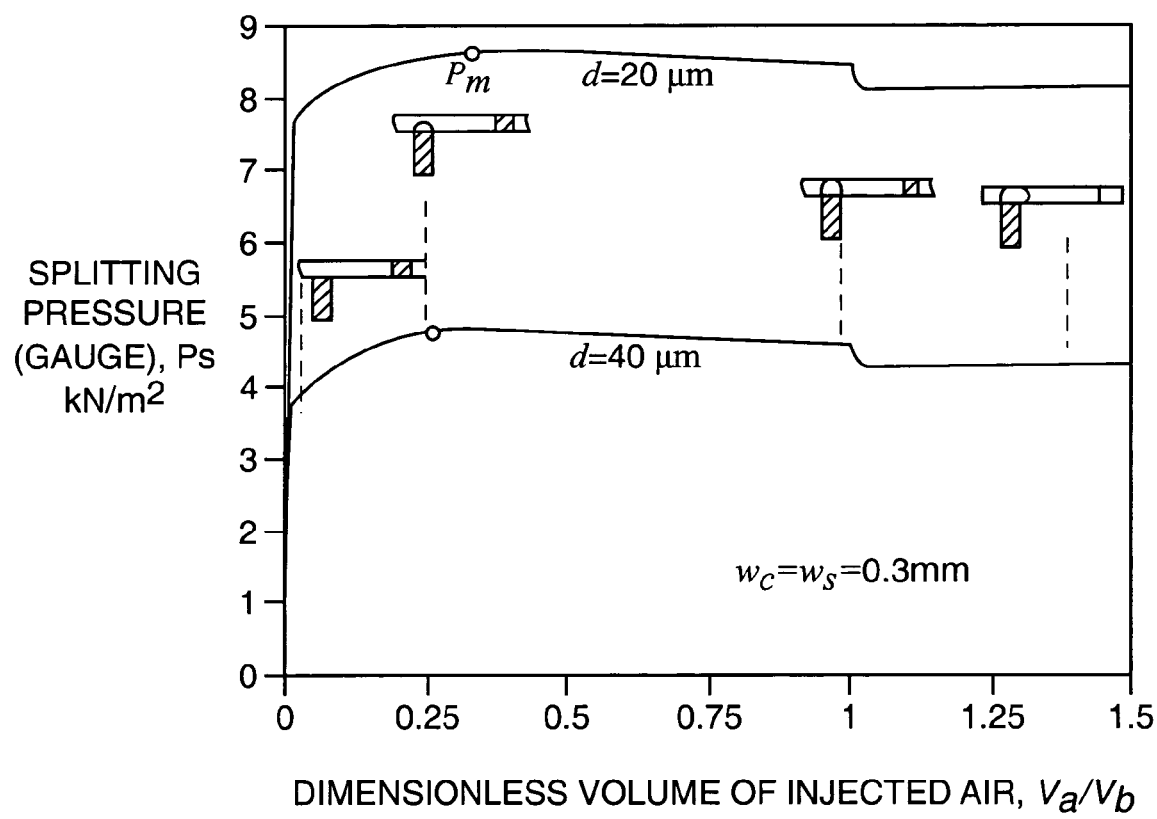
Figure 12A:
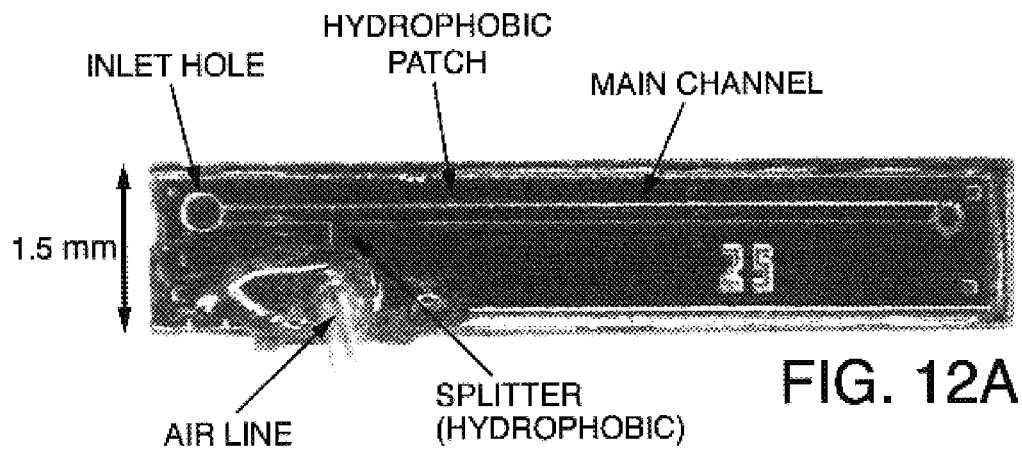
FIGS. 12(A-E) show photographs of a nanoliter liquid metering device. (A) shows a photograph of the device and (B-E) show the progressive generation of a microdroplet.
Figure 12B:
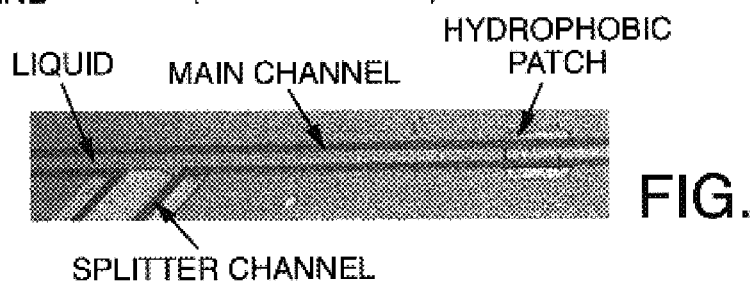
Figure 12C:
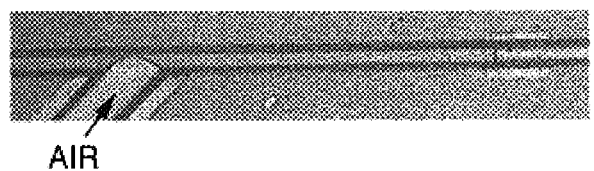
Figure 12D:
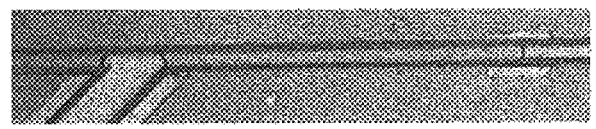
Figure 12E:
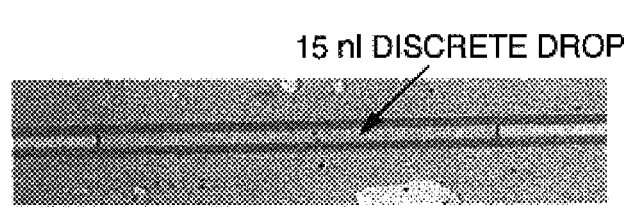

The splitting of liquid in the microchannel is caused by the air pressure induced-growth of an air bubble at the splitting junction As demonstrated by FIG. 11A, the liquid interfacial pressures of the splitting liquid drop can be estimated knowing the instantaneous shape of the liquid-splitting air bubble and the advancing liquid front. FIG. 11B shows that the splitting pressure may be determined from the interface pressures and plotted as a function of air volume injected. The x-axis is made dimensionless by dividing the volume of injected air by the volume of a bubble at the point of liquid splitting. The surface tension ($\sigma=72$ mN/m) and contact angle values ($\theta_r=30°$ and $\theta_p=100°$) correspond to that of water. The pressure requirements for metering, $P_s$, can be estimated by studying the shape of the air-liquid interface of the growing bubble and the advancing front of the liquid. The pressure difference is given by:

$$P_s - P_{atm} = 2\sigma\left[\frac{1}{R_{c,r}} - \frac{1}{R_{c,a}}\right], \quad (12)$$

where $R_{c,r}$ and $R_{c,a}$ are the radius of curvature of the receding and the advancing liquid interfaces respectively.

The mean radius of curvature of receding liquid interface, $R_{c,r}$ will vary as the air bubble grows and can be estimated from the principal radius of curvatures as:

$$R_{c,r} = 2\left[\frac{1}{R_{c,r\|}} + \frac{1}{R_{c,r\perp}}\right]^{-1}. \quad (13)$$

In the above expression, $R_{c,r\|}$ and $R_{c,r\perp}$ are the principal radii of curvature in the plane of the microchannel device and its orthogonal plane, respectively. As air is injected into the splitter channel, the liquid interface at the hydrophobic splitting channel changes from a flat surface ($R_{c,r\|}=R_{c,r\perp}=\infty$) to a cylindrical shape:

$$\left(R_{c,r\|} = \infty \text{ and } R_{c,r\perp} = \frac{d}{2\cos\theta_r}\right).$$

Further air introduction will cause the interface to curve in the plane of the channel as well:

$$\left(R_{c,r\|} = \frac{w_b^2 + \frac{w_s^2}{4}}{2w_b}, R_{c,r\perp} = \frac{d}{2\cos\theta_r}\right).$$

The radius $R_{c,r\|}$ will vary as the bubble (width, $w_b$) grows. After the discrete drop is split ($w_b=w_c$), the receding interface shape will assume the shape of a bent cylinder with a contact angle $\theta_r$ maintained at all the walls:

$$\left(\Rightarrow R_{c,r\|} = \frac{w_c}{2\cos\theta_r} \text{ and } R_{c,r\perp} = \frac{d}{2\cos\theta_r}\right).$$

Note that the above mechanism of bubble growth is assumed based on the experimental observation that a threshold pressure is required before any bubble curvature is observed in the plane of the channel.

FIG. 12 presents, in addition to a liquid-stopping hydrophobic patch in the microchannel, a hydrophobic splitter channel, which is pressurized to split a liquid drop. A sequence of close-up photographs (FIG. 12B-E) show liquid being stopped at the hydrophobic patch and metering of a discrete drop due to application of air pressure at the splitter junction. The volume of the metered drop is determined by the product of L, the distance between the hydrophobic patch and the splitter junction and A, the cross-sectional area of the channel. Therefore, the bubble surface must be bending in the plane perpendicular to the channel before it bends in the plane of the microchannel (FIG. 12C).

The mean radius of curvature of the advancing liquid front, $R_{c,a}$ remains constant during the splitting process and is given by Equations (2) and (7). Note that the advancing liquid is in the hydrophobic part of the channel ($\theta_p > 90°$) and therefore $R_{c,a}$ is negative.

The pressure required to split a drop can therefore be estimated from the channel dimensions ($w_c$, $w_s$ and d), hydrophilic and hydrophobic contact angles and the surface tension of the liquid. We have calculated this pressure as a function of volume of air injected, as shown in FIG. 1B, for two different channel depths. As can be seen from the figure, each of the pressure profile has a maximum pressure, termed the metering pressure ($P_m$). $P_m$ is given by the following relationship:

$$P_m - P_{atm} = 2\sigma\left[\frac{1}{w_s} + \frac{\cos\theta_r}{d} - \cos\theta_p\left(\frac{1}{w_c} + \frac{1}{d}\right)\right]. \quad (14)$$

Please note that $P_s=P_m$ when the width of the bubble equals half the splitter width ($w_b=w_s/2$). In order to successfully meter a drop, a pressure greater than the metering pressure must be applied. The metering pressure is strongly dependent on the reciprocal of the channel depth, ranging from 2.5 kN/m² for a 100 μm deep channel to 150 kN/m² (>1 atmosphere) for a one micrometer deep channel.

Figure 13A:
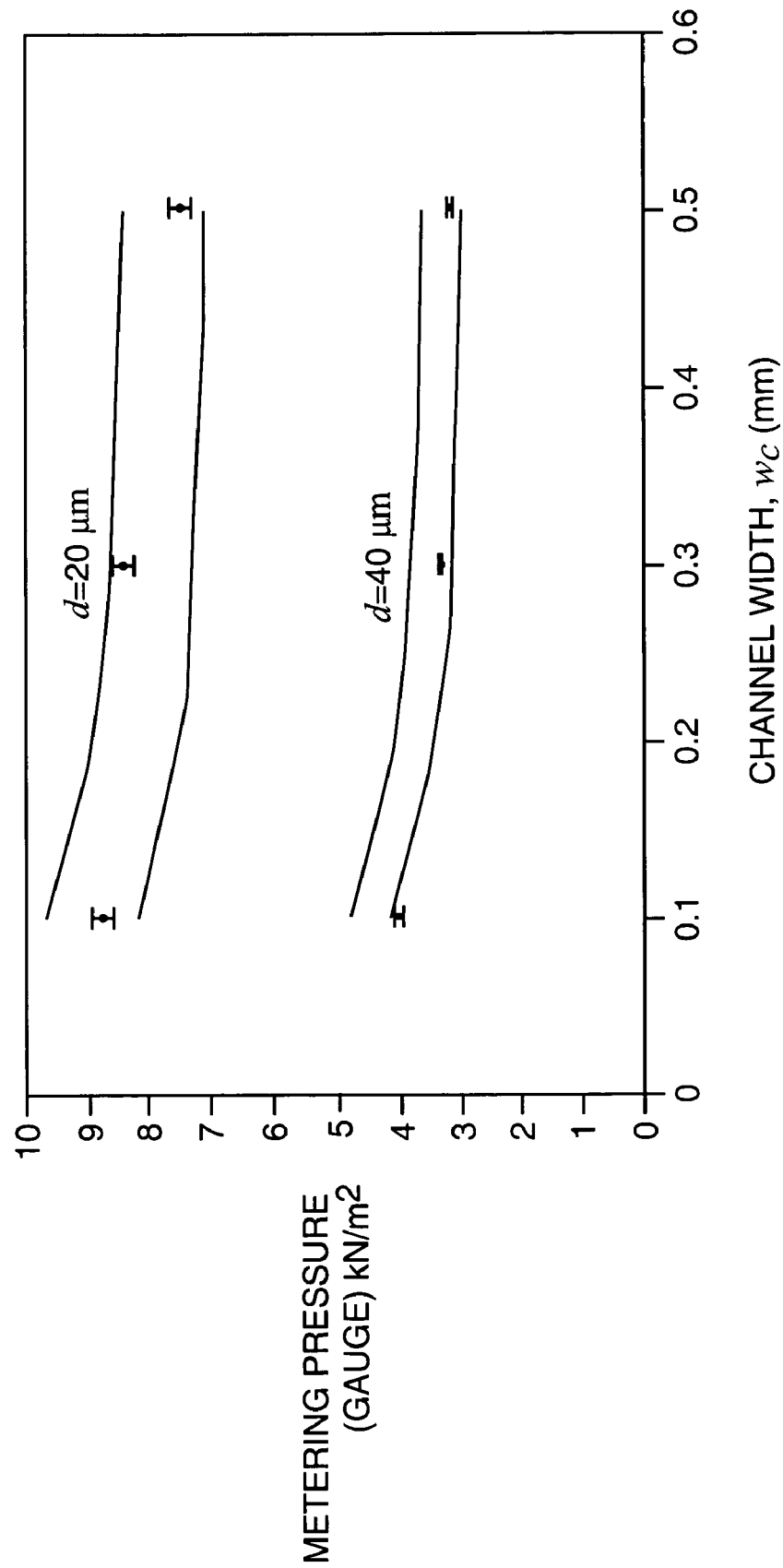
FIGS. 13(A & B) show experimental metering pressures measured in different microchannel devices, varying in channel depth and width.
Figure 13B:
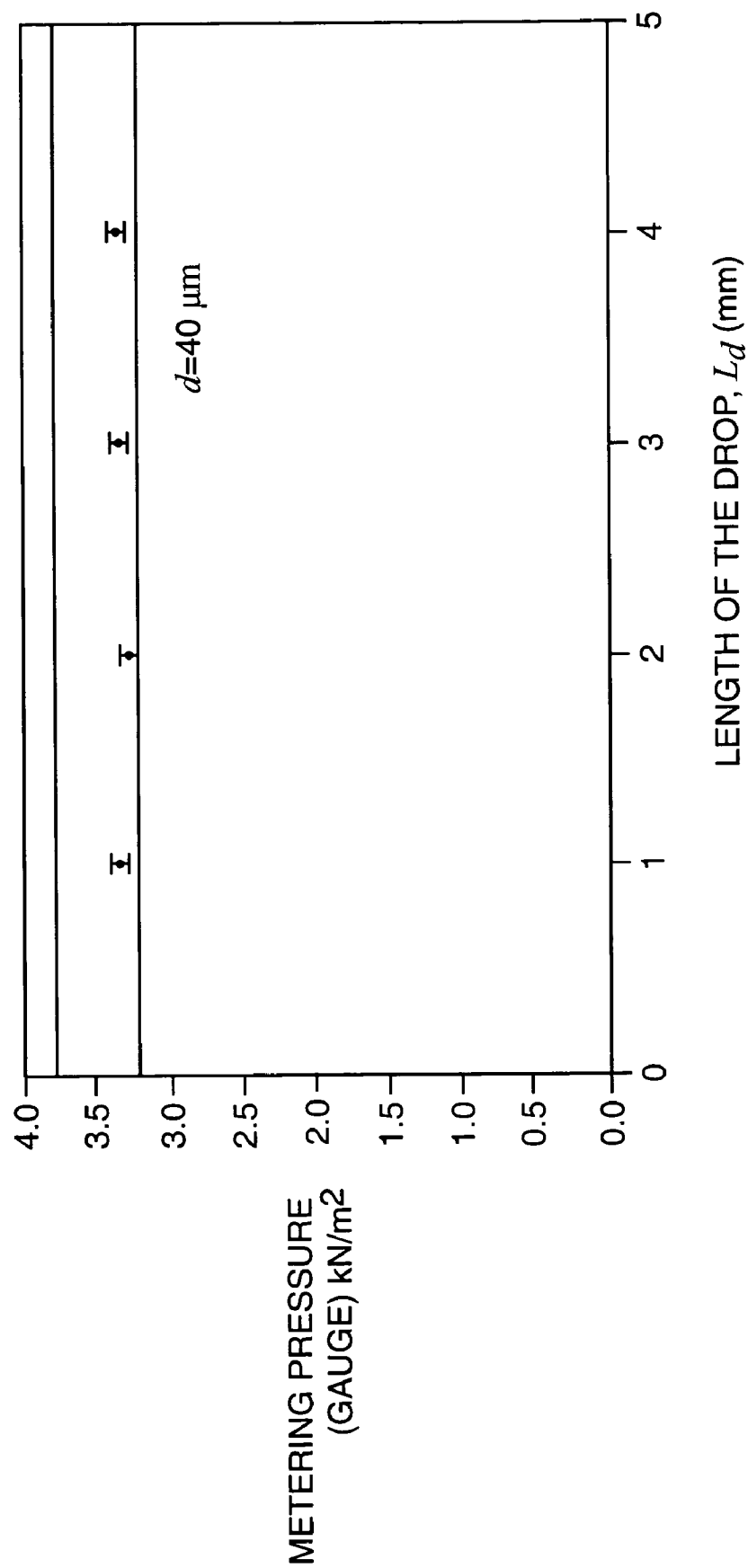

As presented in FIG. 13A, the error bar in metering pressure for each microchannel device represents different experiments performed in the same microchannel device. The theoretical estimates are plotted as two solid lines because the exact value of channel depth (after assembly) and the incipient contact angles are not known. An error of ±1 μm is used for the channel depth and an error of ±5° is used for the contact angles. As shown in FIG. 13B the metering pressure is independent of the drop length, as seen in microchannel devices where the length of the drop is varied from 1 to 4 mm.

Experiments performed to measure metering pressures ($P_m$) show a strong dependence on the channel depth (FIG. 13B), as predicted by the theory. Experimental metering pressures varied from 3.5 kN/m² for a 40 μm deep channel to 9 kN/m² for a 20 μm deep channel. Increasing the channel width increases the radius of curvatures of the liquid interfaces and thereby, reduces the metering pressure. The length of the drop (1-5 mm) has no effect on the pressure drop (FIG. 13B).

The measured metering pressures may be compared with the theoretical predictions described earlier. In order to predict metering pressures in a microchannel (known $w_c$, d and $w_s$), precise values of the liquid contact angles ($\theta_r$ and $\theta_p$) are required. Liquid contact angle values can vary from the static contact angle by 5-10° during incipient motion, as in metering. Due to inherent difficulty in measuring the actual contact angle values, we have used the static contact angle values measured earlier ($\theta_r=30°$ and $\theta_p=100°$) with an error of 5° to calculate the theoretical bounds of metering pressures in different microchannels (FIG. 13). The measured metering pressures lie within the bounds of the theoretical limits.

In addition to changing the channel height, the metering pressures can also be tailored by varying the dimension of the splitting channel ($w_s$). In the above discussions, the splitter width was maintained comparable to the main channel dimension. Decreasing the width of the splitter channel will make the initial size of the air bubble smaller, thereby increasing the pressure required to form a bubble. On the other hand, increasing the splitter width wider than the main channel will flatten the splitting pressure profile.

Figure 14:
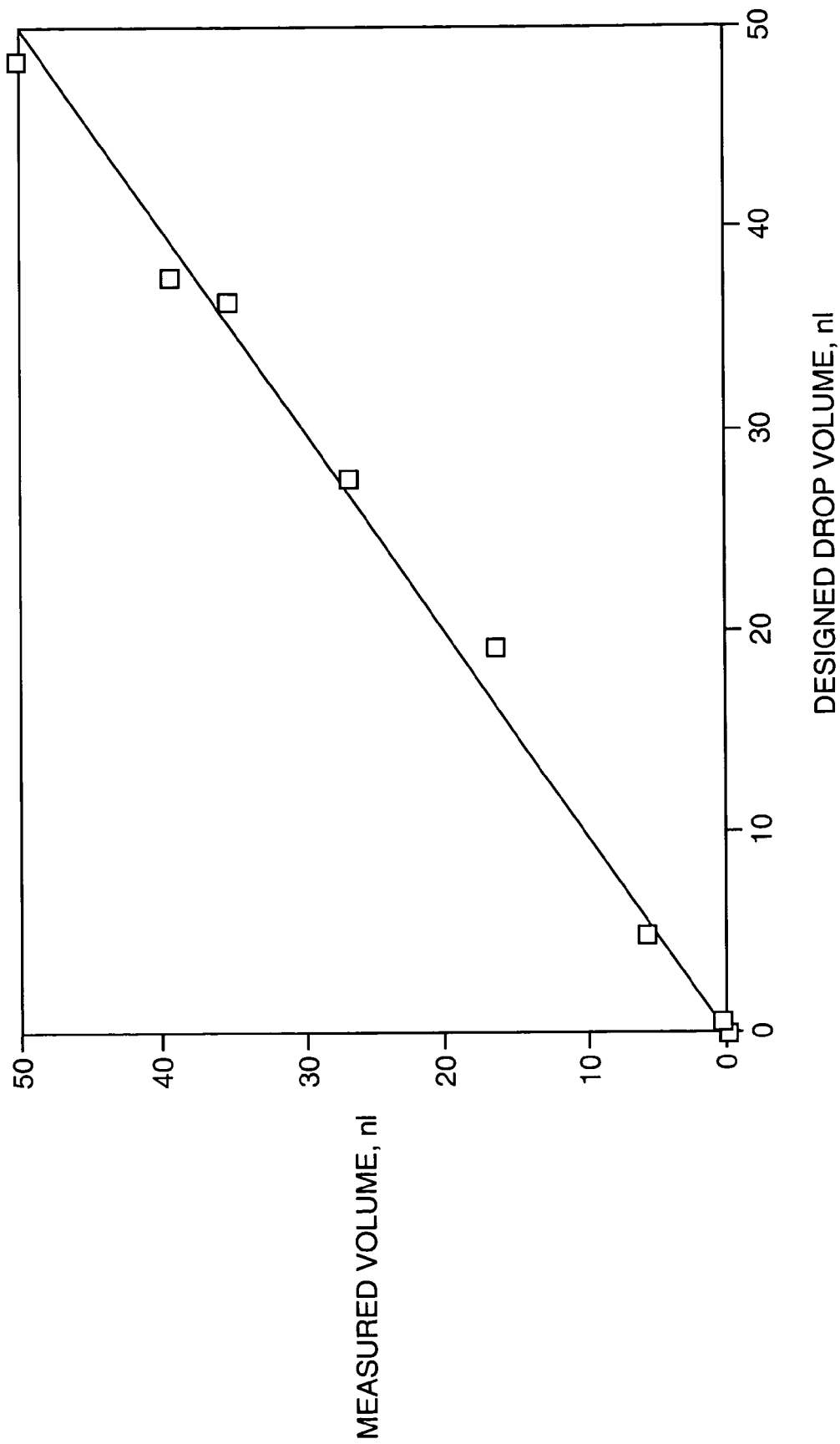
FIG. 14 shows measured drop volume plotted as a function of nominal drop volume in different channel designs.

The volume of the metered drop is determined by the product of $L_d$, the distance between the center of the splitter junction to the edge of the hydrophobic patch, and the cross-sectional area of the channel. The dependence of the drop volume on geometry of the metering device allows metering of pre-determined size drops with high accuracy. This has been verified experimentally by metering drops in different channels to split volumes ranging from 0.1 to 120 nanoliters with high accuracy (FIG. 14). The cross-section of the channels varied from 0.001 $mm^2$ to 0.025 $mm^2$, the drop length varied from 0.5 to 5 mm.

The absolute error in the volume of the metered drop can be estimated and will be on the order of the size of an air bubble pinned to the splitter channel and touching the opposite wall. The relative error in metering will therefore depend on the size of the splitting junction and the length of the drop. The error in metering decreases with a decrease in the splitter junction and increase in the drop length. Therefore highly accurate drop volumes can be metered by narrowing the splitter junction for a given drop length.

VII. Microfabrication of Ancillary Devices

Since the use of convection cell devices may be supplemented by the addition of ancillary devices and control mechanisms (for example, for the movement of solutions and reagents to and from the convection cells), the description of the preferred embodiments includes: A) microfabrication techniques for manufacture of silicone-based devices, and; B) channel treatment for optimum flow and reproducibility.

A. Microfabrication of Silicone-Based Devices

As noted previously, silicone has well-known fabrication characteristics and associated photographic reproduction techniques. The principal modern method for fabricating semiconductor integrated circuits is the so-called planar process. The planar process relies on the unique characteristics of silicone and comprises a complex sequence of manufacturing steps involving deposition, oxidation, photolithography, diffusion and/or ion implantation, and metallization, to fabricate a "layered" integrated circuit device in a silicone substrate. See e.g., W. Miller, U.S. Pat. No. 5,091,328, hereby incorporated by reference.

For example, oxidation of a crystalline silicone substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicone wafer. Electrical interconnection and contact to the various p or n regions that make up the integrated circuit is made by a deposition of a thin film of conductive material, usually aluminum or polysilicone, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

In a preferred embodiment, channels were prepared on 500 μm thick glass wafers (Dow Corning 7740) using standard aqueous-based etch procedures. The initial glass surface was cleaned and received two layers of electron beam evaporated metal (20 nm chromium followed by 50 nm gold). Photoresist Microposit 1813 (Shipley Co.) was applied 4000 rpm, 30 seconds; patterned using glass mask 1 and developed. The metal layers were etched in chromium etchant (Cr-14, Cyantek Inc.) and gold etchant (Gold Etchant TFA, Transene Co.) until the pattern was clearly visible on the glass surface. The accessible glass was then etched in a solution of hydrofluoric acid and water (1:1, v/v). Etch rates were estimated using test wafers, with the final etch typically giving channel depths of 20 to 30 μm. For each wafer, the depth of the finished channel was determined using a surface profilometer. The final stripping (PRS-2000, J. T. Baker) removed both the remaining photoresist material and the overlying metal.

In one embodiment, channels etched on glass in the above-described manner, were bonded to the heater-element wafer in a two-part construction approach using optical adhesive (SK-9 Lens Bond, Sumers Laboratories, Fort Washington, Pa.). The bond was cured under an ultraviolet light source (365 nm) for 12 to 24 hours.

Figure 15A:
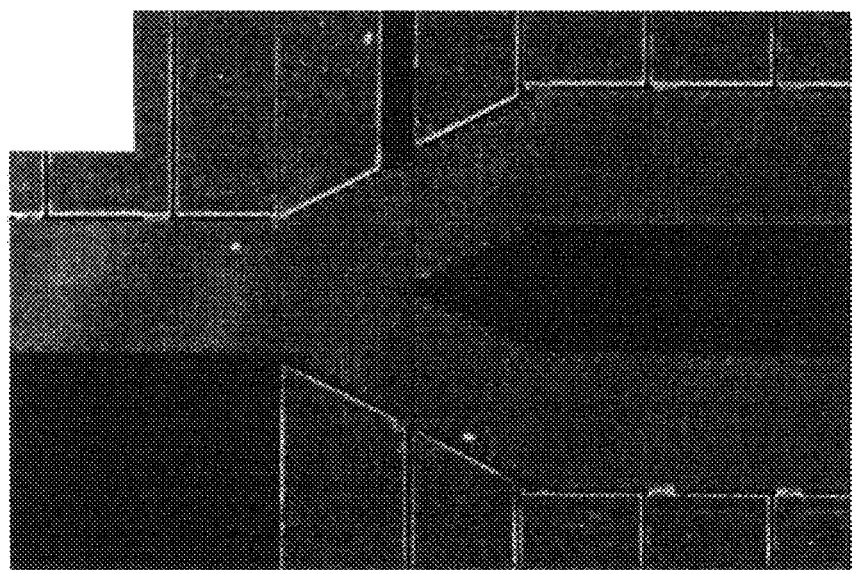
FIG. 15 shows (A) a photomicrograph of inlay-process heater elements on the surface on a silicone wafer, (B) a scanning micrograph (SEM) of an inlay-process heater wire in cross section (the arrows indicate the deposited aluminum, silicon dioxide and silicon nitride layers) and, (C) is a SEM of a channel formed on glass using a wet-etch process, shown in cross section with the etched face of the wager immediately adjacent to the intersection of two channels.
Figure 15B:
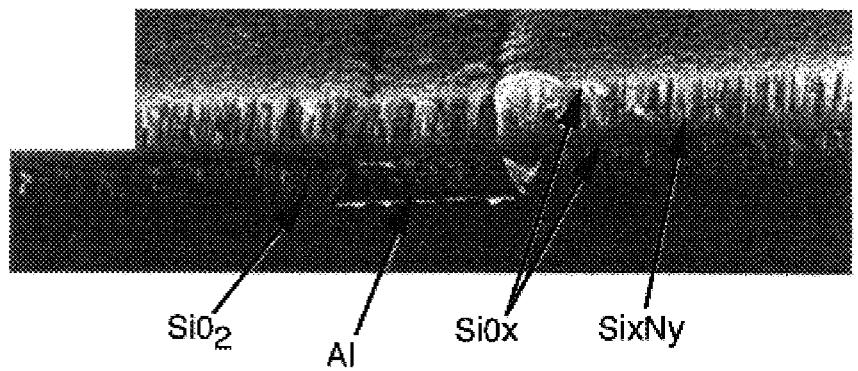

Initial device design by the present inventors involved single layers of silicone. However, experience showed these to be inadequate to prevent short circuiting due to (necessary) liquid microdroplets within the channels (see experiments described below). The preferred design involves a triple layer of oxides. Such a preferred device capable of moving and mixing nanoliter droplets was constructed by bonding a planar silicone substrate to channels etched in a glass cover. A series of metal heaters was inlaid on the silicone substrate as two parallel lanes merging into a single lane (a "Y"-shape) (FIG. 15A). The heating elements were formed by first coating the wafer with a 1.0 μm layer of thermal silicon dioxide. Next, 0.35 μm deep, 5 μm wide grooves were reactive-ion etched (RIE) into the silicon dioxide following the pattern set in an overlying photoresist. Aluminum was deposited (0.35 μm) across the entire wafer using electron beam evaporation and the metal layer was "lifted-off" from all surfaces having intact photoresist using a stripping solution. The metal inlay process gives a relatively planar surface and provides a uniform base for deposition of a solution-impermeable barrier layer. The barrier layer is made by a sequence of three plasma-enhanced chemical vapor depositions (PECVD): 1.0 μm silicon oxide ($SiO_x$), 0.25 μm silicon nitride ($Si_xN_y$), and 1.0 μm silicon oxide ($SiO_x$) (FIG. 15B). Some heating elements were also used as resistive temperature sensors.

Heater elements may be necessary in the present invention to initiate and maintain the convective flow field. Heater elements may be fabricated, for example, as follows. Silicon wafer (p-type, 18-22½-cm, ⟨100⟩, boron concentration Å $10^{15}$ $cm^{-3}$) was used as a substrate for growth of $SiO_2$ thermal oxide (1 μm); photoresist (AZ-5214-E, Hoescht-Celanese) was applied and spun at 3000 rpm, 30 seconds. The resist was patterned (metal 1) and developed. Reactive ion etch (RIE, PlasmaTherm, Inc.) was performed to 0.35 μm depth into the $SiO_2$ layer at the following conditions: $CHF_3$, 15 sccm (standard cubic centimeters per minute); $CF_4$, 15 sccm; 4 mTorr; DC bias voltage of 200V, 100 W, 20 minutes. The etch depth was measured by profilometer and 0.35 μm metallic aluminum was electron beam deposited. The resist and overlying metal was lifted off by development using Microposit 1112A remover in solution (Shipley Co.). The barrier layers consist of sequentially deposited 1 μm $SiO_x$, 0.25 μm $Si_xN_y$, and 1 μm $SiO_x$ using plasma-enhanced chemical vapor deposition (PECVD). RIE was used to etch contact holes to the metal layer using a second mask ($CHF_3$, 15 sccm; $CF_4$, 15 sccm; 4 mTorr; and DC bias voltage of 200V, 100 W, 120 minutes).

Figure 15C:
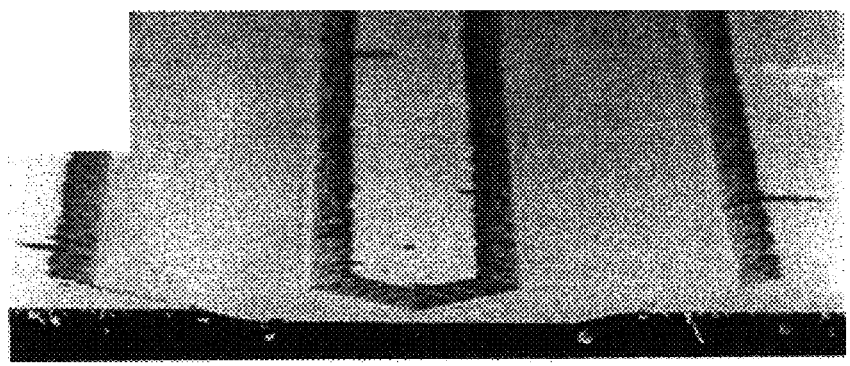

As shown in FIG. 15, the elements are arrayed as two parallel lanes, each 500 μm wide, merging into one lane. The individual heaters consist of paired aluminum wires (5 μm) winding across the 500 μm wide region. The broad metal areas on either side of the elements are bonding locations for connection to external circuitry. The width of the aluminum element is 5 μm. The channel in FIG. 15C has identical width and design configurations as the heating element lanes in FIG. 15A, and is uniformly etched 500 μm wide and approximately 20 μm deep.

The heating-element wafer was bonded to a glass wafer containing etched channels with the same "Y" format. An aqueous chemical etch of concentrated hydrofluoric acid was used to produce channels with defined side walls and uniform depth. The etched channels are defined by a chromium/gold mask and are 500 μm wide and approximately 20 μm deep. The complementary silicon heater and glass channel wafers were aligned and then bonded with adhesive to form the finished device.

Each heating element used as a temperature sensor is preferably first calibrated by measurement of electrical resistance at 22° C. and 65° C. under constant voltage; intermediate temperatures are estimated by linear interpolation.

B. Channel Treatment with Hydrophilic Enhancing Compounds

Prior to performing microdroplet motion and biological reactions, the channels are preferably treated by washing with base, acid, buffer, water and a hydrophilicity-enhancing compound, followed by a relatively high concentration solution of non-specific protein. In a preferred embodiment, the channels are washed with approximately 100 μl each of the following solutions in series: 0.1N NaOH; 0.1N HCl; 10 mM Tris-HCl (pH 8.0), deionized $H_2O$, Rain-X Anti-Fog (a hydrophilicity-enhancing compound commercially available from Unelko Corp., Scottsdale, Ariz.), and 500 μg/μl bovine serum albumin (non-specific protein commercially available in restriction enzyme grade from GIBCO-BRL). The wafer was placed on a stereoscope stage (Olympus SZ1145), and the contact pads for the heating elements were connected to a regulated power supply. Heating occurred by passing approximately 30 volts through the element in short pulses and observing the movement rate of the droplets. A detectable reduction in droplet volume from evaporation was noted in each experiment, usually of less than 30%. Droplet movement was recorded with a Hamamatsu video camera on videotape.

EXAMPLES

The following example(s) serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade).

Example 1

Convective flow fields are ubiquitous in nature and play a central role in a wide variety of transport processes occurring in the Earth's atmosphere and oceans, as well as in industrial processes involving chemical reactions, heat transfer and crystal growth (Chandrasekhar, S., *Hydrodynamic and Hydromagnetic Stability* Claredon, Oxford, 1961). Of particular interest from both experimental and theoretical standpoints is the case of Rayleigh-Bénard convection, which arises as a consequence of a buoyancy driven instability in a confined horizontal fluid layer heated from below. Here, the dimensionless Rayleigh number Ra expresses the interplay between buoyant forces driving the instability and diffusive restoring forces acting in opposition.

$$Ra = \frac{ga(T_2 - T_1)h^3}{nk}$$

Here, a is the coefficient of thermal expansion of the fluid, g is the acceleration due to gravity, $T_1$ and $T_2$ are the temperatures at the top and bottom surfaces of the cavity respectively, h is the height of the cavity, n is the kinetic viscosity and k is the thermal diffusivity.

The inherent structure of Rayleigh-Bénard convection, steady circulatory flow between surfaces maintained at two fixed temperatures, is ideally suited for performing thermally activated chemical reactions which require temperature cycling such as the polymerase chain reaction (PCR). We have developed a novel device and method employing the circulatory flow field established by Rayleigh-Bénard convection to perform PCR amplification of DNA inside a 35 ml cylindrical cavity. Temperature cycling is achieved as the flow field continually shuttles fluid packets vertically through the temperature zones associated with denaturation (~95° C.) and annealing/extension (60-70° C.), eliminating the dynamic external temperature control required in conventional thermocyclers. Amplification proceeds through thermal equilibration of convected fluid packets with their surroundings as various spatial locations within the cavity. In order for RB-PCR to perform efficiently, a steady circulatory flow field must be generated that engages the entire reaction volume yet is slow enough that sufficient time is spent within each temperature zone to allow the corresponding reactions to reach completion. The parameters available to control the fluid motion are the Rayleigh-Bénard convective flow, the reactions are performed in aqueous solution thereby fixing the fluid properties, and the temperature difference is set by the annealing/extension and denaturing temperatures applied at the upper and lower surfaces of the RB-PCR cell, respectively. Hence, the Rayleigh number can only be changed by varying the height of the cavity, leaving geometry as the primary flow control parameter.

Figure 16A:
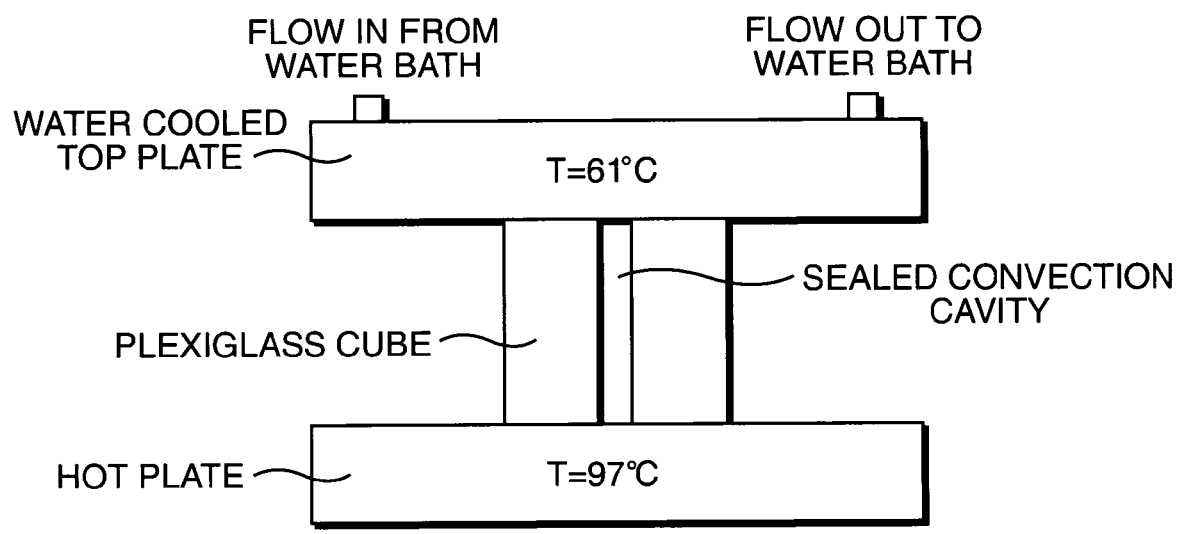
FIG. 16 shows (A) a RB-PCR cell schematic, (B) influence of geometry on Rayleigh-Bénard convection and, (C) DNA amplification in RB-PCR cell.
Figure 16B:
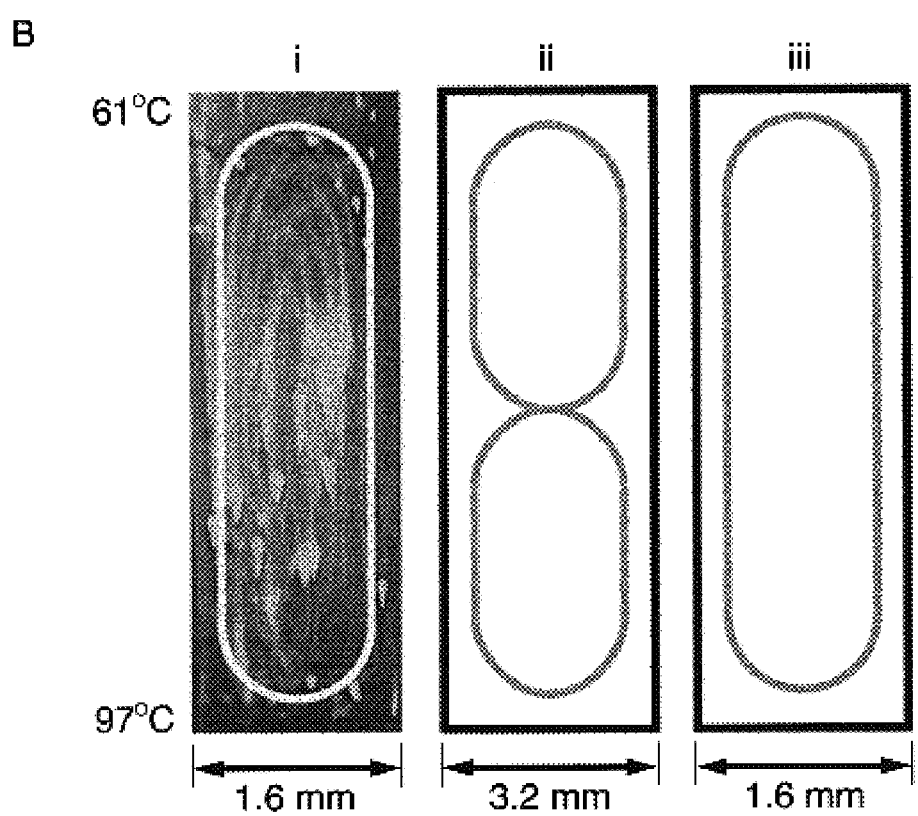

We constructed a series of Rayleigh-Bénard convection cells by drilling holes in Plexiglas cubes and imaged the resulting flow patterns by recording the motion of an aqueous suspension of fluorescent latex microspheres (FIG. 16A). At values of Ra of order $10^5$, the convection motion is characterized by steady flow within a single well-defined axisymmetric cellular pattern. Increasing Ra to the vicinity of $10^6$ while holding h/d constant (h/d equals the height/diameter aspect ratio) causes the flow velocity to increase, ultimately inducing a transition to an unsteady flow regime. We also investigated the effect of adjusting the aspect ratio of the cavity as an alternative means of controlling the flow. Holding the Rayleigh number constant in the vicinity of $10^6$ while increasing h/d reverses the unsteady flow transition and restores uniform convective motion. These observations are in qualitative agreement with the results of Müller and coworkers (Muller, G., et al., *J. Cryst. Growth* 70:78, 1984) and suggest a considerable amount of tunability to accommodate a variety of reaction conditions and reagent volumes. Specifically, FIG. 16B shows the influence of geometry on Rayleigh-Bénard convection (Lindahl, T., and B. Nyberg, *Biochemistry* 11:3610, 1972). The convection cavities oriented vertically and the top and bottom of each image corresponds to the top and bottom surfaces of the cavities, maintained at $T_1=61°$ C. and $T_2=97°$ C., respectively. (i) h/d=3.3, Ra=4.6×10$^5$; steady circulatory convective flow between the top and bottom of the cavity. (ii) h/d=3.3, Ra=3.7×10$^6$; unsteady convective flow characterized by a "figure-8" pattern whose crossover point location continually varies with time. (iii) h/d=6.3, Ra=3.7×10$^6$; steady convective flow is re-established at the same value of Ra as in (ii). Rayleigh numbers are computed based on physical properties of water at 80° C.

Motion of a dilute aqueous suspension of fluorescent latex microspheres (6 μm diameter; Polysciences) was observed through a fluorescent stereoscope, imaged using an intensified charge-coupled device camera and recorded to videotape. Averaging the digitized video stream over a time interval of 1 sec. produced particle paths representative of microsphere trajectories.

Based on flow visualization studies in a number of geometrices, we selected cavities 1.5 cm in height with h/d~10 for PCR experiments because of their characteristically slow flow velocities which permit adequate time to be spent within each temperature zone. The PCR mixture was subjected to convective flow generated with top and bottom surfaces of the cavity maintained at 61° C. and 97° C., respectively. The bottom surface temperature was maintained with a heat source (e.g., a hot plate) while the top surface temperature was maintained by circulating water from a water bath maintained at the correct temperature. Approximately 9 ng/ml of human DNA template was used and the target was a 295 bp (base pair) fragment of the single-copy beta-actin gene.

Figure 16C:
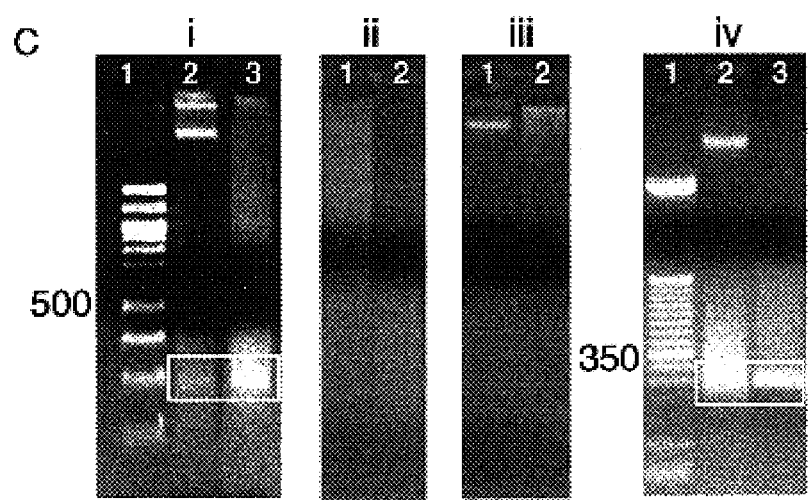

Briefly, a 295-bp segment of the human β-Actin gene was amplified. Forward and reverse primer sequences were 5'-TCACCCACAATGTGCCCATCTACGA-3' (SEQ ID NO: 1) and 5'-CAGCGAACCGCTCATTGCCAATGG-3' (SEQ ID NO: 2). Reactions contained 10 mM Tris-HCL (pH 8.3); 50 mM KCL; 4 mM MgCl$_2$; 0.2 mM each dATP, dGTP, dCTP and dUTP; 9 ng/μl human DNA and 0.1 U/μl of AmpliTaq Polymerase (PE Applied Biosystems). Reactions were run for about 1.5 hours, aspirated from the reaction chambers, stained with SYBR-Green 1 (final concentration 200×) and run on a 1% Agarose gel at 110 V for 1 hour. As shown in FIG. 16C, the Rayleigh-Bénard cell was capable of producing an amplification product of the correct size and compares well with the PCR product generated in a thermocycler under similar temperature conditions. In addition to enzyme concentration, the reaction was sensitive to incubation time and the temperature at the top surface of the cell.

This successful demonstration of DNA amplification in a RB-PCR cell shows that Rayleigh-Bénard convection can serve as a useful platform to perform a variety of chemical and biochemical reactions which require temperature cycling. The system is exceedingly simple and may be easily assembled in any laboratory. The potential versatility of this system may be better realized through more thorough characterization, both theoretical and experimental, of convective flow fields in high aspect ratio cavities and studies to optimize PCR in flowing systems. Addressing these issues presents a unique opportunity to attain an improved understanding of the fundamental physical processes governing PCR in static and flowing systems alike, while achieving DNA amplification in a greatly simplified experimental format. Specifically, FIG. 16C shows the result of DNA amplification in RB-PCR cell. The top and bottom surfaces of the cavity are maintained at $T_1=61°$ C. and $T_2=97°$ C., respectively. Human genomic DNA was used as template. (i) Amplification with 0.1 U/mL AmpliTaq Polymerase. Lane 1: 100 bp ladder, Lane 2: PCR product from RB-PCR cell, Lane 3: PCR product generated in a thermocycler using two-temperature cycling (denature: 95° C., anneal 61° C., 40 cycles). (ii) Negative control with no enzyme. Lane: 1 RB-PCR cell product, Lane 2: thermocycler product. (iii) Negative control with no enzyme. Lane 1: RB-PCR cell product, Lane 2: thermocycler product. (iv) Amplification with 0.15 u/mL AmpliTaq Polymerase. Lane 1: 50 bp ladder, Lane 2: PCR product from RB-PCR cell Lane 3: PCR product generated in a thermocycler using two-temperature cycling (denature: 95° C., anneal 61° C., 40 cycles). The intense high-migrating band observed in the RB-PCR positive reactions and template-containing negative control in likely to be an effect of high-temperature at the bottom of the cell (97° C.) causing single-stranded scission of the >50 kb template DNA fragments (Lindahl, T., and B. Nyberg, *Biochemistry* 11:3610, 1972). A faint band is also observed at the same migration distance in positive reactions and template-containing negative controls generated in the thermocycler but does not appear in the photographs.

What is claimed is:

1. A method, comprising:
  a) providing:
    i) a plurality of reaction vessels having a top and a bottom configured with an aspect ratio of at least 3.3, wherein said ratio is defined as vessel height divided by vessel diameter,
    ii) a heat source contacting said bottom of said reaction vessels;
    iii) a cooling means contacting said top of said reaction vessels; and,
    iv) a solution comprising a plurality of reactants;
  b) introducing said solution into a first reaction vessel comprising a first temperature differential between said top and said bottom, wherein
    i) said first temperature differential is produced by simultaneously heating said bottom with said heat source and cooling said top with said cooling means,
    ii) said heating produces spatially uniform temperature and temporally uniform temperature across said fluid in said top of said reaction vessel, and
    iii) said cooling produces spatially uniform temperature and temporally uniform temperature across said fluid in said bottom of said reaction vessel;
  c) transferring said solution from said first reaction vessel to a second reaction vessel wherein said second reaction vessel comprises a second temperature differential between said top and said bottom; and;
  d) transferring said solution from said second reaction vessel to said first reaction vessel under such conditions that said plurality of reactants form a reactant product.

2. The method of claim 1, wherein, in cross section, said reaction vessels are without corners.

3. The method of claim 1, wherein, in cross section, said reaction vessels are with corners.

4. The method of claim 1, wherein said reactants comprise i) nucleic acid comprising a target and ii) primers substantially homologous to at least a portion of said target.

5. The method of claim 1, wherein said reactant product comprise amplified nucleic acid.

6. The method of claim 1, wherein said reaction vessels comprise material selected from the group consisting of Plexiglas™, glass, plastics, silicones and metal.

7. The method of claim 1, wherein said reaction vessel is part of an array.

8. The method of claim 1, wherein said first temperature differential of at least 10° C. is established within said convection cell.

9. The method of claim 1, further providing at least one microdroplet channel wherein said microdroplet channel is in fluid communication with said reaction vessels.

10. A method, comprising:
  a) providing:
    i) a plurality of reaction vessels comprising a top and a bottom;
    ii) a heat source contacting said bottom of said reaction vessels;
    iii) an active cooling means contacting said top of said reaction vessels; and
    iv) a solution comprising a plurality of nucleic acids comprising a target and a primer substantially homologous to at least a portion of said target;
  b) introducing said solution into a first reaction vessel comprising a first temperature differential between said top and said bottom, wherein
    i) said first temperature differential is produced by simultaneously heating said bottom with said heat source and cooling said top with said cooling means,
    ii) said heating produces spatially uniform temperature and temporally uniform temperature across said fluid in said top of said reaction vessel, and
    iii) said cooling produces spatially uniform temperature and temporally uniform temperature across said fluid in said bottom of said reaction vessel;
  c) transferring said solution from said first reaction vessel to a second reaction vessel wherein said second reaction vessel comprises a second temperature differential between said top and said bottom; and
  d) transferring said solution from said second reaction vessel to said first reaction vessel under such conditions that said nucleic acids form an amplified nucleic acid.

11. The method of claim 10, wherein said reaction vessels comprise at least one material selected from the group consisting of Plexiglas™, glass, plastics, silicones and metal.

12. The method of claim 10, wherein said reaction vessels are part of an array.

13. The method of claim 10, wherein a temperature differential of at least 5° C. is established between said top surface and said bottom surface.

14. The method of claim 10, also providing at least one microdroplet channel wherein said microdroplet channel is in fluid communication with said reaction vessel.

15. A method, comprising:
  a) providing:
    i) a plurality of reaction vessels comprising a top and a bottom;

ii) a heat source contacting said bottom of said reaction vessels, and
iii) a solution comprising a plurality of reactants;
b) introducing said solution into a first reaction vessel comprising a first temperature differential between said top and said bottom, wherein
   i) said first temperature differential is produced by simultaneously heating said bottom with said heat source and cooling said top with said cooling means,
   ii) said heating produces spatially uniform temperature and temporally uniform temperature across said fluid in said top of said reaction vessel, and
   iii) said cooling produces spatially uniform temperature and temporally uniform temperature across said fluid in said bottom of said reaction vessel;
c) transferring said solution from said first reaction vessel to a second reaction vessel wherein said second reaction vessel comprises a second temperature differential between said top and said bottom; and,
d) transferring said solution from said second reaction vessel to said first reaction vessel under conditions such that said reactants form a reactant product.

16. The method of claim 15, wherein said reactants comprise i) nucleic acid comprising a target and ii) primers substantially homologous to at least a portion of said target.

17. The method of claim 15, wherein said reactant product comprises amplified nucleic acid.

18. The method of claim 15, wherein said reaction vessels comprise material selected from the group consisting of Plexiglas™, glass, plastics, silicones and metal.

19. The method of claim 15, wherein said reaction vessels are part of an array.

20. The method of claim 17, wherein said second temperature differential is at least 5° C.

21. The method of claim 17, wherein said first temperature differential is at least 10° C.

22. The method of claim 17, further providing at least one microdroplet channel wherein said microdroplet channel is in fluid communication with said reaction vessel.

23. A method, comprising:
a) providing:
   i) a plurality of reaction vessels having a top and a bottom configured with an aspect ratio of at least 3.3, wherein said ratio is defined as vessel height divided by vessel diameter,
   ii) a heat source contacting said bottom of said reaction vessels,
   iii) a cooling means contacting said top of said reaction vessels, and,
   iv) a solution comprising a plurality of reactants,
b) introducing said solution into a reaction vessel, and
c) simultaneously heating said bottom with said heat source and cooling said top with said cooling means to produce a temperature differential between said top and said bottom, wherein
   i) said heating produces spatially uniform temperature and temporally uniform temperature across said fluid in said top of said reaction vessel, and
   ii) said cooling produces spatially uniform temperature and temporally uniform temperature across said fluid in said bottom of said reaction vessel.

24. A method, comprising:
a) providing:
   i) a plurality of reaction vessels comprising a top and a bottom,
   ii) a heat source contacting said bottom of said reaction vessels,
   iii) an active cooling means contacting said top of said reaction vessels, and
   iv) a solution comprising a plurality of nucleic acids comprising a target and a primer substantially homologous to at least a portion of said target;
b) introducing said solution into a reaction vessel;
c) simultaneously heating said bottom with said heat source and cooling said top with said cooling means to produce a temperature differential between said top and said bottom, wherein
   i) said heating produces spatially uniform temperature and temporally uniform temperature across said fluid in said top of said reaction vessel,
   ii) said cooling produces spatially uniform temperature and temporally uniform temperature across said fluid in said bottom of said reaction, and
   iii) said target nucleic acid is amplified.

25. A method, comprising:
a) providing:
   i) a plurality of reaction vessels comprising a top and a bottom,
   ii) a heat source contacting said bottom of said reaction vessels, and
   iii) a solution comprising a plurality of reactants,
b) introducing said solution into a reaction vessel,
c) simultaneously heating said bottom with said heat source and cooling said top with said cooling means to produce a temperature differential between said top and said bottom, wherein
   i) said heating produces spatially uniform temperature and temporally uniform temperature across said fluid in said top of said reaction vessel,
   ii) said cooling produces spatially uniform temperature and temporally uniform temperature across said fluid in said bottom of said reaction vessel, and
   iii) said reactants form a reactant product.

26. The method of claim 1, wherein said first reaction vessel is selected from the group consisting of circular vessel and oval vessel.

27. The method of claim 10, wherein said first reaction vessel is selected from the group consisting of circular vessel and oval vessel.

28. The method of claim 15, wherein said first reaction vessel is selected from the group consisting of circular vessel and oval vessel.

29. The method of claim 23, wherein said reaction vessel is selected from the group consisting of circular vessel and oval vessel.

30. The method of claim 24, wherein said reaction vessel is selected from the group consisting of circular vessel and oval vessel.

31. The method of claim 25, wherein said reaction vessel is selected from the group consisting of circular vessel and oval vessel.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic -continued

<400> SEQUENCE: 1
tcacccacaa tgtgcccatc tacga                                             25

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
cagcgaaccg ctcattgcca atgg                                              24